US010420833B2

(12) United States Patent
Trent et al.

(10) Patent No.: US 10,420,833 B2
(45) Date of Patent: Sep. 24, 2019

(54) COMBINATORIAL PLATFORM FOR THE DISPLAY OF SURFACE ADJUVANTS AND ANTIGENS

(71) Applicant: BOARD OF REGENTS, THE UNIVERSITY OF TEXAS SYSTEM, Austin, TX (US)

(72) Inventors: M. Stephen Trent, Cedar Park, TX (US); Joseph M. Boll, Austin, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 15/311,233

(22) PCT Filed: May 18, 2015

(86) PCT No.: PCT/US2015/031325
§ 371 (c)(1),
(2) Date: Feb. 13, 2017

(87) PCT Pub. No.: WO2015/179270
PCT Pub. Date: Nov. 26, 2015

(65) Prior Publication Data
US 2017/0080080 A1 Mar. 23, 2017

Related U.S. Application Data

(60) Provisional application No. 62/000,254, filed on May 19, 2014.

(51) Int. Cl.
C12N 7/00 (2006.01)
C12N 9/10 (2006.01)
A61K 39/00 (2006.01)
A61K 39/02 (2006.01)
A61K 39/12 (2006.01)
C12N 15/52 (2006.01)
A61K 39/145 (2006.01)
C07K 14/005 (2006.01)
C07K 14/195 (2006.01)
G01N 33/53 (2006.01)

(52) U.S. Cl.
CPC .......... A61K 39/145 (2013.01); A61K 39/107 (2013.01); A61K 39/12 (2013.01); C07K 14/005 (2013.01); C07K 14/195 (2013.01); C12N 7/00 (2013.01); C12N 9/1081 (2013.01); C12N 15/52 (2013.01); C12Y 204/99019 (2015.07); A61K 2039/522 (2013.01); A61K 2039/5252 (2013.01); A61K 2039/55572 (2013.01); A61K 2039/55583 (2013.01); A61K 2039/575 (2013.01); A61K 2039/6006 (2013.01); A61K 2039/6087 (2013.01); A61K 2039/62 (2013.01); A61K 2039/70 (2013.01); C07K 2319/03 (2013.01); C07K 2319/21 (2013.01); C07K 2319/42 (2013.01); C07K 2319/91 (2013.01); C12N 2760/16022 (2013.01); C12N 2760/16034 (2013.01); C12N 2760/16071 (2013.01); C12N 2760/16134 (2013.01); Y02A 50/401 (2018.01); Y02A 50/407 (2018.01); Y02A 50/466 (2018.01); Y02A 50/484 (2018.01)

(58) Field of Classification Search
None
See application file for complete search history.

(56) References Cited

U.S. PATENT DOCUMENTS

| 4,436,727 | A | 3/1984 | Ribi |
| 5,348,867 | A | 9/1994 | Georgiou et al. |
| 6,491,919 | B2 | 12/2002 | Crane |
| 7,384,645 | B2 | 6/2008 | Foster et al. |
| 7,622,128 | B2 | 11/2009 | Darveau et al. |
| 8,048,433 | B2 | 11/2011 | Tommassen et al. |
| 8,945,587 | B2 | 2/2015 | Trent et al. |
| 2003/0215464 | A1 | 11/2003 | Klimpel et al. |
| 2013/0230555 | A1 | 9/2013 | Trent et al. |

FOREIGN PATENT DOCUMENTS

| WO | WO 2011/113003 | * | 1/2011 | ............... C12N 1/20 |
| WO | WO 2011/113003 | | 9/2011 | |
| WO | WO 2013/130779 | | 9/2013 | |
| WO | WO 2013/159234 | | 10/2013 | |

OTHER PUBLICATIONS

Herrera et al., (Mol. Microbio. 2010. vol. 76(6): 1444-1460).*
Mardola et al. Journal of Bacteriology, vol. 177, No. 19, Oct. 1995.*
Casella and Mitchell. "Putting endotoxin to work for us: monophosphoryl lipid A as a safe and effective vaccine adjuvant." *Cellular and molecular life sciences* 65.20 (2008): 3231.
Chen et al. "Delivery of foreign antigens by engineered outer membrane vesicle vaccines." *Proceedings of the National Academy Sciences* 107.7 (2010): 3099-3104.
Cognet, et al., "Expression of recombinant proteins in a lipid A mutant of *Escherichia coli* BL21 with a strongly reduced capacity to induce dendritic cell activation and maturation," *Journal of Immunological Methods*, 272:199-210, 2003.
Gujrati et al. "Bioengineered bacterial outer membrane vesicles as cell-specific drug-delivery vehicles for cancer therapy." *ACS nano* 8.2 (2014): 1525-1537.
Herrera, et al., "Activation of PmrA inhibits LpxT-dependent phosphorylation of lipid A promoting resistance to antimicrobial peptides," *Molecular Microbiology*, 76:1444-60, 2010.

(Continued)

Primary Examiner — Jana A Hines
Assistant Examiner — Khatol S Shahnan Shah
(74) Attorney, Agent, or Firm — Parker Highlander PLLC

(57) ABSTRACT

Engineered bacteria are provided that produce modified lipid A and a polypeptide or polysaccharide antigens. In some aspects, immunogenic compositions are provided comprising a modified a lipid A and a polypeptide or polysaccharide antigen.

12 Claims, 12 Drawing Sheets
Specification includes a Sequence Listing.

(56) References Cited

OTHER PUBLICATIONS

Izquierdo et al. "Synthesis of a Klebsiella pneumoniae O-antigen heteropolysaccharide (O12) requires an ABC 2 transporter," *Journal of bacteriology* 185.5 (2003): 1634-1641.

Liu and Reeves. "*Escherichia coli* K12 regains its O antigen." *Microbiology* 140.1 (1994): 49-57.

Manning et al. "Molecular cloning and expression in *Escherichia coli* K-12 of the O antigens of the Inaba and Ogawa serotypes of the Vibrio cholerae O1 lipopolysaccharides and their potential for vaccine development." *Infection and Immunity* 53.2 (1986):272-277.

Miller et al. "Conjugate meningococcal vaccines development: GSK biologicals experience." *Advances in preventive medicine* 2011 (2011).

Needham and Trent. "Fortifying the barrier: the impact of lipid A remodelling on bacterial pathogenesis." *Nature Reviews Microbiology* 11.7 (2013): 467-481.

Needham, et al., "Modulating the innate immune response by combinatiorial engineering of endotoxin," *PNAS*, 110:1464-9, 2013.

Park, et al., "The structural basis of lipopolysaccharide recognition by the TLR4-MD-2 complex," *Nature*, 458:1191-5, 2009.

PCT International Preliminary Report on Patentability, issued in Application No. PCT/US2015/031325, dated Dec. 1, 2016.

PCT International Search Report and Written Opinion, issued in Application No. PCT/US2013/028281, dated May 22, 2013.

PCT International Search Report and Written Opinion, issued in Application No. PCT/US2015/031325, dated Nov. 4, 2015.

Raetz et al. "Lipid A modification systems in gram-negative bacteria." *Annu. Rev. Biochem.* 76 (2007): 295-329.

Steel et al. "Influenza virus vaccine based on the conserved hemagglutinin stalk domain," *MBio* 1.1 (2010): e00018-10.

Touzé, et al., "Periplasmic phosphorylation of lipid A is linked to the synthesis of undecaprenyl phosphate," *Molecular Microbiology*, 67:264-77, 2008.

* cited by examiner

H1N1 HA2 domain Puerto Rico/8/1934

Coding sequence

5'-
ATGGGTCTGTTTGGCGCTATTGCGGGTTTTATTGAAGGCGGTTGGACGGGCATGATTGACGGTTGGTATGGCTATCACCACCAGAACGAAC
AGGGCTCAGGTTATGCGGCCGATCAGAAATCGACCCAAAACGCTATTAATGGCATCACCAACAAAGTCAATAACGGTGATTGAAAAAATGAA
CATCCAAGATACCGCGACGGGTAAACTGAACGTATGGAAAAAGTTGATGACGGCTTCCTGGA
TATTTGGACCTATAACGCTGAACTGCTGGTCCTGCTGGAAAATGAACGCACGCTGGATTTTCATGACAGCAACGTGAAAAACCTGTACGAA
AAAGTTAAATCTCAGTGTACCTATGACTGACTACCCGAAATACGATGAATCGCAAACTGAATCGCGAAAAAGGCTCAGCCGGTTCGGCAGCTGCGG
ATGCAGACACCATTTGTATCGGCTACCATGGCGAAGATAGCCACGGCTCTGCAAACTCGGTTGACACGTTCTCCGCCTATCAAAACACCCCG
CGTTAATCTGCTGGAAGATAGCCACGGCTCTGCAAACTCGGTTGACACGTTCTCCGCCTATCAAAACACCCCG
ACGTCCGTTCCGAAAACTGCGACGGTCTGGTAACATTCCGAAACATTGGTGCTGCGGAACTGGAACACCACCACCATTAA
-3'

Peptide Sequence

MGLFGAIAGFIEGGWTGMIDGWYGYHHQNEQGSGYAADQKSTQNAINGITNKVNTVIEKMNIQDTATGKEFNKDEKRMENLNKKVDDGFL
DIWTYNAELLVLLENERTLDFHDSNVKNLYEKVKSQLKNNAKEIGNGCFEFYHKCDNECMESVRNGTYDYPKYSEESKLNREKGSAGSAAA
DADTICIGYHANNSTDTVDTVLEKNVTVTHSVNLLEDSHGSANSSLPYQNTHPTTNGESPKYVRSAKLRMVTGLRNIPKLAALEHHHHHH
*

FIG. 3A

H3N2 HA2 domain Hong Kong/68

Coding sequence

ATGGGTCTCTGTTTGGCGCTATTGCGGGCTTCATCGAAAACGGTTGGGAAGGCATGATTGATGGTTGGTATGGCTTTCGTCATCAGAATAGCG
AAGGCACGGCCAAGGCCGGCCAGCTGAAATCTACGCAGGCAGCTATTGACCAAAATCAACGGCCAAATCGAATCGTGTCATTGAAAAAACCAA
CGAAAAAGATCACCAGATCGAAAAAGAATTTAGCGAAGATGAAGGTCGCATTCAAGACCTGGAAAAAATATGTTGAAGATACGAAAATCGA
CCTGTGGAGTTACAACGCCGAACTGCTGTCGCACTGTGCTGAAATCAGCAGCATACCATTGACGAGGACTGATCGATCGAAATGAACAAACTGTTCGAA
AAAACCCGTCGCCAGCTGCGCCTGAGAAATGGCTGCTTCAAAATCTATCATAAATGCGATAACGCATGTGTATTGAAA
GCATCCGCAATGGCACCTATGACTCACGACGTGTACCGTGCCATCAGCGGGTGCCGAATGGCCACCCTGTTAAAACCATTACGATGACCAGATGCGAAGTCACCAAGC
TCTACCGCTACGCTGTCTGCGGCCTCTGGCCAAGCTCTGCAAACACCCCTGAAACTGGCAACGGGTATGCGCAACGGGGCGCCACGCCG
AAATACGTTAAACAAAACCCCTGAAACTGGCAACGGGTATGCGCAACGGGGCGCCACGCCG

Peptide Sequence

MGLFGATAGFTENGWEGMIDGWYGFRHQNSEGTGQAADLKSTQAAIDQINGKLNRVIEKTNEKDHQIEKEFSEDEGRIQDLEKYVEDTKIDL
WSYNAELLVALENQHTIDLTDSEMNKLFEKTRRQLRENAEEMGNGCFKIYHKCDNACIESIRNGTYDHDVYRDEALNNRFQGSAGSAGDNS
TATLCLGHHAVPNGTLVKTITDDQIEVTNATELVQSSGSAGSANDKPFQNTNKETTGATPKYVKQNTLKLATGMRKLAALEHHHHHH*

FIG. 3B

```
Day 0         Day 28         Day 42         Day 44         Day 51
Vaccination   Boost          Serum          Influenza      Sacrifice;
              Vaccination    Collection     Challenge      lung viral
                                                           titers
```

FIG. 3C

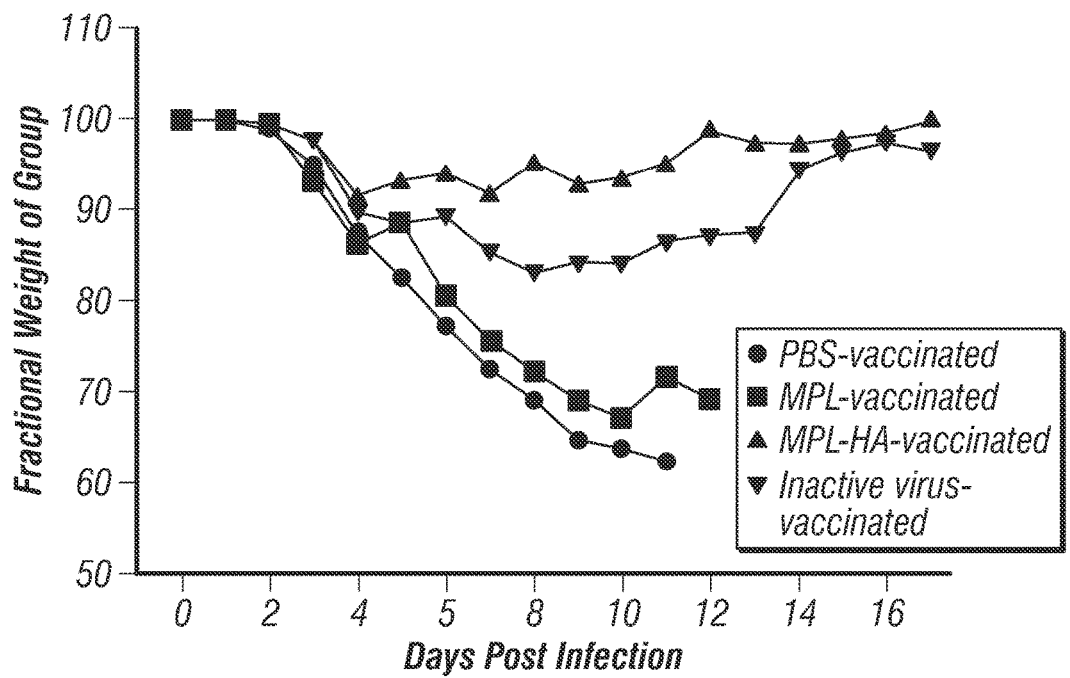
*FIG. 5A*
PBS-vaccinated
*FIG. 5B*
MPL-vaccinated
*FIG. 5C*

MPL-HA-vaccinated

Inactive virus-vaccinated

SEQUENCE LISTING

<160> NUMBER OF SEQ ID NOS: 16

<210> SEQ ID NO 1
<211> LENGTH: 26
<212> TYPE: DNA
<213> ORGANISM: Artificial sequence
<220> FEATURE:
<223> OTHER INFORMATION: Synthetic primer

<400> SEQUENCE: 1
gcggatccat gctcaaacag acatta                                    26

<210> SEQ ID NO 2
<211> LENGTH: 28
<212> TYPE: DNA
<213> ORGANISM: Artificial sequence
<220> FEATURE:
<223> OTHER INFORMATION: Synthetic primer

<400> SEQUENCE: 2
gcgcggccgc ctaaataatc tctctatt                                  28

<210> SEQ ID NO 3
<211> LENGTH: 26
<212> TYPE: DNA
<213> ORGANISM: Artificial sequence
<220> FEATURE:
<223> OTHER INFORMATION: Synthetic primer

<400> SEQUENCE: 3
gcggatcctt ggcaagattt catatc                                    26

<210> SEQ ID NO 4
<211> LENGTH: 28
<212> TYPE: DNA
<213> ORGANISM: Artificial sequence
<220> FEATURE:
<223> OTHER INFORMATION: Synthetic primer

<400> SEQUENCE: 4
gcgcggccgc tcaatattct tttttacg                                  28

<210> SEQ ID NO 5
<211> LENGTH: 26
<212> TYPE: DNA
<213> ORGANISM: Artificial sequence
<220> FEATURE:
<223> OTHER INFORMATION: Synthetic primer

<400> SEQUENCE: 5
gcggatccat gtatatgaag agaata                                    26

<210> SEQ ID NO 6
<211> LENGTH: 28
<212> TYPE: DNA
<213> ORGANISM: Artificial sequence
<220> FEATURE:
<223> OTHER INFORMATION: Synthetic primer

<400> SEQUENCE: 6
gcgcggccgc tcagaaatta taactaat                                  28

<210> SEQ ID NO 7
<211> LENGTH: 26
<212> TYPE: DNA
<213> ORGANISM: Artificial sequence
<220> FEATURE:
<223> OTHER INFORMATION: Synthetic primer

<400> SEQUENCE: 7
gcgaattcat gttcgcagca atcatt                                   26

<210> SEQ ID NO 8
<211> LENGTH: 26
<212> TYPE: DNA
<213> ORGANISM: Artificial sequence
<220> FEATURE:
<223> OTHER INFORMATION: Synthetic primer

<400> SEQUENCE: 8
gcggatcctc agaggaggct gaaaag                                   26

<210> SEQ ID NO 9
<211> LENGTH: 26
<212> TYPE: DNA
<213> ORGANISM: Artificial sequence
<220> FEATURE:
<223> OTHER INFORMATION: Synthetic primer

<400> SEQUENCE: 9
gcggatccat gaacgtgagt aaatat                                   26

<210> SEQ ID NO 10
<211> LENGTH: 28
<212> TYPE: DNA
<213> ORGANISM: Artificial sequence
<220> FEATURE:
<223> OTHER INFORMATION: Synthetic primer

<400> SEQUENCE: 10
gcgcggccgc tcaaaactga aagcgcat                                 28

<210> SEQ ID NO 11
<211> LENGTH: 26
<212> TYPE: DNA
<213> ORGANISM: Artificial sequence
<220> FEATURE:
<223> OTHER INFORMATION: Synthetic primer

<400> SEQUENCE: 11
gcggatccat gaacaaatac agctat                                   26

<210> SEQ ID NO 12
<211> LENGTH: 28
<212> TYPE: DNA
<213> ORGANISM: Artificial sequence
<220> FEATURE:
<223> OTHER INFORMATION: Synthetic primer

<400> SEQUENCE: 12
gcgcggccgc tcagaagaag aaggtgat                                 28

<210> SEQ ID NO 13
<211> LENGTH: 819
<212> TYPE: DNA
<213> ORGANISM: Influenza A virus

<400> SEQUENCE: 13

```
atgggtctgt ttggcgctat tgcgggtttt attgaaggcg gttggacggg catgattgac    60
ggttggtatg gctatcacca ccagaacgaa cagggctcag gttatgcggc cgatcagaaa   120
tcgacccaaa acgctattaa tggcatcacc aacaaagtca atacggtgat gaaaaaatg    180
aacatccaag ataccgcgac gggtaaagaa tttaacaaag acgaaaaacg tatggaaaac   240
ctgaacaaaa aagttgatga cggcttcctg gatatttgga cctataacgc tgaactgctg   300
gtcctgctgg aaaatgaacg cacgctggat tttcatgaca gcaacgtgaa aaacctgtac   360
gaaaaagtta atctcagct gaaaaacaac gcgaaagaaa tcggcaacgg ttgcttcgaa    420
ttttaccaca aatgcgataa cgaatgtatg gaaagcgtgc gtaatggtac ctatgactac   480
ccgaaataca gtgaagaatc caaactgaat cgcgaaaaag gctcagccgg ttcggcagct   540
gcggatgcag acaccatttg tatcggctac catgccaaca attcaaccga tacggttgac   600
acggtcctgg agaaaaacgt gaccgttacg cattccgtta atctgctgga agatagccac   660
ggctctgcca acagctctct gccgtatcaa aacacccacc cgaccacgaa tggtgaaagt   720
ccgaaatacg tccgttccgc aaaactgcgc atggtgacgg tctgcgtaa cattccgaaa    780
ctggctgcgg cactggaaca ccatcaccac caccattaa                         819
```

<210> SEQ ID NO 14
<211> LENGTH: 272
<212> TYPE: PRT
<213> ORGANISM: Influenza A virus

<400> SEQUENCE: 14

```
Met Gly Leu Phe Gly Ala Ile Ala Gly Phe Ile Glu Gly Gly Trp Thr
 1               5                  10                  15

Gly Met Ile Asp Gly Trp Tyr Gly Tyr His His Gln Asn Glu Gln Gly
            20                  25                  30

Ser Gly Tyr Ala Ala Asp Gln Lys Ser Thr Gln Asn Ala Ile Asn Gly
        35                  40                  45

Ile Thr Asn Lys Val Asn Thr Val Ile Glu Lys Met Asn Ile Gln Asp
    50                  55                  60

Thr Ala Thr Gly Lys Glu Phe Asn Lys Asp Glu Lys Arg Met Glu Asn
65                  70                  75                  80

Leu Asn Lys Lys Val Asp Asp Gly Phe Leu Asp Ile Trp Thr Tyr Asn
                85                  90                  95

Ala Glu Leu Leu Val Leu Leu Glu Asn Glu Arg Thr Leu Asp Phe His
            100                 105                 110

Asp Ser Asn Val Lys Asn Leu Tyr Glu Lys Val Lys Ser Gln Leu Lys
        115                 120                 125

Asn Asn Ala Lys Glu Ile Gly Asn Gly Cys Phe Glu Phe Tyr His Lys
    130                 135                 140

Cys Asp Asn Glu Cys Met Glu Ser Val Arg Asn Gly Thr Tyr Asp Tyr
145                 150                 155                 160

Pro Lys Tyr Ser Glu Glu Ser Lys Leu Asn Arg Glu Lys Gly Ser Ala
                165                 170                 175

Gly Ser Ala Ala Ala Asp Ala Asp Thr Ile Cys Ile Gly Tyr His Ala
            180                 185                 190

Asn Asn Ser Thr Asp Thr Val Asp Thr Val Leu Glu Lys Asn Val Thr
        195                 200                 205

Val Thr His Ser Val Asn Leu Leu Glu Asp Ser His Gly Ser Ala Asn
    210                 215                 220
```

Ser Ser Leu Pro Tyr Gln Asn Thr His Pro Thr Asn Gly Glu Ser
225                 230                 235                 240

Pro Lys Tyr Val Arg Ser Ala Lys Leu Arg Met Val Thr Gly Leu Arg
            245                 250                 255

Asn Ile Pro Lys Leu Ala Ala Ala Leu Glu His His His His His His
        260                 265                 270

<210> SEQ ID NO 15
<211> LENGTH: 816
<212> TYPE: DNA
<213> ORGANISM: Influenza A virus

<400> SEQUENCE: 15
atgggtctgt ttggcgctat tgcgggcttc atcgaaaacg gttgggaagg catgattgat      60
ggttggtatg gctttcgtca tcagaatagc gaaggcaccg ccaagcggc cgatctgaaa     120
tctacgcagg cagctattga ccaaatcaac ggcaaactga atcgtgtcat gaaaaaacc     180
aacgaaaaag atcaccagat cgaaaaagaa tttagcgaag atgaaggtcg cattcaagac     240
ctggaaaaat atgttgaaga tacgaaaatc gacctgtgga gttacaacgc cgaactgctg     300
gtcgcactgg aaaatcagca taccattgat ctgacggact ccgaaatgaa caaactgttc     360
gaaaaaccc gtcgccagct gcgtgaaaac gctgaagaaa tgggtaatgg ctgcttcaaa     420
atctatcata atgcgataa cgcatgtatt gaaagcatcc gcaatggcac ctatgatcac     480
gacgtgtacc gtgatgaagc cctgaacaat cgctttcagg gtagtgccgg ctccgcaggt     540
gacaactcta ccgctacgct gtgtctgggc atcacgcgg tgccgaatgg caccctggtt     600
aaaaccatta cggatgacca gatcgaagtc accaacgcga cggaactggt gcaaagctct     660
ggctcagctg gttcggcgaa tgataaaccg tttcagaaca ccaataaaga aaccacgggc     720
gccacgccga aatacgttaa acaaaacacc ctgaaactgg caacgggtat gcgtaaactg     780
gcggcggcgc tggaacatca ccatcaccat cactaa                                816

<210> SEQ ID NO 16
<211> LENGTH: 271
<212> TYPE: PRT
<213> ORGANISM: Influenza A virus

<400> SEQUENCE: 16

Met Gly Leu Phe Gly Ala Ile Ala Gly Phe Ile Glu Asn Gly Trp Glu
1               5                   10                  15

Gly Met Ile Asp Gly Trp Tyr Gly Phe Arg His Gln Asn Ser Glu Gly
            20                  25                  30

Thr Gly Gln Ala Ala Asp Leu Lys Ser Thr Gln Ala Ala Ile Asp Gln
        35                  40                  45

Ile Asn Gly Lys Leu Asn Arg Val Ile Glu Lys Thr Asn Glu Lys Asp
    50                  55                  60

His Gln Ile Glu Lys Glu Phe Ser Glu Asp Glu Gly Arg Ile Gln Asp
65                  70                  75                  80

Leu Glu Lys Tyr Val Glu Asp Thr Lys Ile Asp Leu Trp Ser Tyr Asn
                85                  90                  95

Ala Glu Leu Leu Val Ala Leu Glu Asn Gln His Thr Ile Asp Leu Thr
            100                 105                 110

Asp Ser Glu Met Asn Lys Leu Phe Glu Lys Thr Arg Arg Gln Leu Arg
        115                 120                 125

Glu Asn Ala Glu Glu Met Gly Asn Gly Cys Phe Lys Ile Tyr His Lys
    130                 135                 140

-continued

```
Cys Asp Asn Ala Cys Ile Glu Ser Ile Arg Asn Gly Thr Tyr Asp His
145                 150                 155                 160

Asp Val Tyr Arg Asp Glu Ala Leu Asn Asn Arg Phe Gln Gly Ser Ala
                165                 170                 175

Gly Ser Ala Gly Asp Asn Ser Thr Ala Thr Leu Cys Leu Gly His His
            180                 185                 190

Ala Val Pro Asn Gly Thr Leu Val Lys Thr Ile Thr Asp Asp Gln Ile
        195                 200                 205

Glu Val Thr Asn Ala Thr Glu Leu Val Gln Ser Ser Gly Ser Ala Gly
    210                 215                 220

Ser Ala Asn Asp Lys Pro Phe Gln Asn Thr Asn Lys Glu Thr Thr Gly
225                 230                 235                 240

Ala Thr Pro Lys Tyr Val Lys Gln Asn Thr Leu Lys Leu Ala Thr Gly
                245                 250                 255

Met Arg Lys Leu Ala Ala Ala Leu Glu His His His His His His
                260                 265                 270
```

COMBINATORIAL PLATFORM FOR THE DISPLAY OF SURFACE ADJUVANTS AND ANTIGENS

The present application is a national phase application under 35 U.S.C. § 371 of International Application No. PCT/US2015/031325, filed May 18, 2015, which claims the priority benefit of United States provisional application number 62/000,254, filed May 19, 2014, the entire contents of which are incorporated herein by reference.

The invention was made with government support under Grant No. R01 AI076322 awarded by the National Institutes of Health. The government has certain rights in the invention.

INCORPORATION OF SEQUENCE LISTING

The sequence listing that is contained in the file named "UTFB1044WO_ST25.txt", which is 10_KB (as measured in Microsoft Windows®) and was created on May 11, 2015, is filed herewith by electronic submission and is incorporated by reference herein.

BACKGROUND OF THE INVENTION

1. Field of the Invention

The present invention relates generally to the field of microbiology. More particularly, it concerns bacterial cell engineering.

2. Description of Related Art

In 1892, Richard Pfeiffer introduced the revolutionary concept of bacterial endotoxin in his description of a non-proteinaceous, non-secreted toxin bound to the surface of *Vibrio cholerae* (Pfeiffer et al., 1892). This toxin, now known as lipopolysaccharide (LPS), is the major surface molecule of Gram-negative bacteria that triggers the host immune response during infection (Poltorak et al., 2000; Raetz et al., 2002). LPS is composed of lipid A, core oligosaccharide, and O-antigen (Raetz et al., 2007). Lipid A is recognized by the innate immune system through the conserved pattern recognition receptor, Toll-like receptor 4/myeloid differentiation factor 2 (TLR4/MD-2) complex, which initiates a robust signal cascade that leads to production of inflammatory cytokines. This signaling is crucial for detection and clearance of infection, but can be potent enough to result in lethal endotoxic shock (Raetz et al., 2002). Such tremendous immunogenicity makes lipid A an attractive therapeutic tool as an adjuvant, but its toxicity is a major concern.

Efforts have been made to dampen the toxicity of whole bacteria by altering the degree of Lipid A acylation. One approach has been to inactivate lpxM, a gene encoding the acyltransferase responsible for converting lipid A from a penta-acylated to a hexa-acylated species. LpxM mutants are under investigation in the development of meningococcal vaccines, oncolytic *Salmonella* strains that specifically target tumors, and bacterial strains designed for gene therapy. Other efforts to detoxify cells or outer membrane vesicles have included acyl chain modification by the enzymes PagL or PagP. However, no bacterial strains have been previously generated using a complex combinatorial approach to yield a diverse library of in bacterium linked lipid A moieties and antigens.

SUMMARY OF THE INVENTION

Provided herein are engineered *E. coli* strains that produce a lipid A moiety linked to an antigen and methods for producing these *E. coli* strains. In some embodiments, an engineered *E. coli* strain is provided that comprises one or more lipid modification polynucleotides selected from the group consisting of lpxE, lpxF, lpxO, lpxR, pagL, and pagP polynucleotides and one or more antigen associated polynucleotides. The lpxE, lpxF, lpxO, lpxR, pagL, and pagP polynucleotides include those described in the Examples below, those described in U.S. Patent Application Publication No. 20130230555, which is hereby incorporated by reference in its entirety, and their homologs, orthologs, and paralogs. In some embodiments, the engineered *E. coli* strain comprises lpxE, pagL and pagP polynucleotides. In other embodiments, the engineered *E. coli* strain comprises lpxE, lpxO, pagL and pagP polynucleotides.

U.S. Patent Application Publication No. 20130230555 describes that combinations of the LpxE, LpxF, LpxO, LpxR, PagL, and PagP endotoxin modification enzymes are used to generate a library of *E. coli* strains, each presenting unique lipid A moieties on its surface. These engineered bacterial cells and lipid A moieties stimulated a wide range of TLR4 activation, resulting in differential cytokine induction. Thus, U.S. Patent Application Publication No. 20130230555 provided the ability to select from a range of inflammation and cytokine induction by lipid A that prior adjuvant options could not provide.

The present disclosure significantly advances this previously described technology by describing compositions and methods for linking an antigen with a lipid A moiety within a bacterium such as *E. coli* and thereby producing a "whole vaccine" from a bacterium. Prior glycoconjugate vaccine production has been tedious because of laborious chemical synthesis, purification, and production costs. The present disclosure reduces these costs dramatically as it allows the generation of an antigen and an adjuvant in parallel and linked with one another in less time with lower costs. In addition, many complex carbohydrate antigens cannot be synthesized in vitro. The present disclosure not only provides compositions and methods for the synthesis of complex carbohydrate antigens in a bacterium such as *E. coli*, but also provides for their synthesis in parallel with numerous lipid A adjuvants.

According to the present disclosure, the lipid modification polynucleotides can reside within a vector introduced into the engineered *E. coli* strain. In some embodiments, the vector is a plasmid and the *E. coli* strain is transformed with the plasmid. In some embodiments, the plasmid is a pACYC184 plasmid, for example, the pACYC184 plasmid as shown in FIG. 1. It is to be understood, however, that the present description also encompasses lipid modification polynucleotides that are integrated into the *E. coli* chromosome. Accordingly, the present invention includes an engineered *E. coli* strain having either or both intra-chromosomal and extrachromosomal lipid modification polynucleotides, including but not limited to, lpxE, lpxF, lpxO, lpxR, pagL, and pagP polynucleotides.

The antigen associated polynucleotides can also reside within a vector introduced into the engineered *E. coli* strain. This vector can be the same or different from the vector containing the lipid modification polynucleotides. In some embodiments, the vector containing the antigen associated polynucleotides is a plasmid and the *E. coli* strain is transformed with the plasmid. It is to be understood, however, that the present description also encompasses antigen associated polynucleotides that are integrated into the *E. coli* chromosome. Accordingly, the present invention includes an engineered *E. coli* strain having either or both intra-chromosomal and extrachromosomal antigen associated polynucleotides.

The antigen associated polynucleotides can be peptide antigen encoding or polysaccharide antigen generating polynucleotides. Peptide antigen encoding polynucleotides include, but are not limited to, those associated with peptide vaccines for the treatment of anthrax, brucellosis, cholera, diphtheria, Hib, Lyme disease, meningococcal infection, pertussis, plague, pneumococcal infection (PCV and PPSV), tetanus, tuberculosis, typhoid, adenovirus, influenza, hantavirus, hepatitis A, hepatitis B, human papilloma virus, encephalitis, measles, mumps, polio, rabies, rotavirus, and related cancers. In one embodiment, the peptide antigen encoding polynucleotides are viral Influenza polynucleotides such as hemagglutinin and/or neuraminidase polynucleotides.

In some embodiments, an Lpp targeting polynucleotide, a transmembrane polynucleotide, and, if necessary, a linker sequence are introduced into the engineered *E. Coli* strain in addition to the one or more lipid modification polynucleotides and the one or more peptide antigen encoding polynucleotides. In these embodiments, the peptide antigen is produced as a fusion protein with the transmembrane polypeptide, which thereby directs the peptide antigen to the outer membrane of an *E. coli* cell. The lipid A moiety and the peptide antigen are thereby co-localized at the outer membrane and can be isolated together in an outer membrane vesicle.

An Lpp targeting polynucleotide comprises nucleotides that encode an Lpp targeting sequence, which targeting sequence includes a signal sequence and about the first nine amino acids of a mature Lpp protein. See U.S. Pat. No. 5,348,867, which is hereby incorporated by reference in its entirety, for exemplary descriptions and sequences of Lpp targeting sequences, transmembrane polypeptides, and linker sequences. One exemplary transmembrane polynucleotide is an ompA polynucleotide. The Lpp targeting polynucleotide, a transmembrane polynucleotide, and, if necessary, the linker sequence can be introduced to the *E. coli* strain in any vector. In some embodiments, these sequences are contained within the same vector that contains the one or more antigen encoding polynucleotides in a position downstream of the transmembrane polynucleotide such that translation of the vector results in a fusion polypeptide comprising an Lpp targeting polypeptide/linker peptide/transmembrane polypeptide/antigen polypeptide.

In some embodiments related to the expression of peptide antigen encoding polynucleotides, the engineered *E. coli* strain is a wild-type *E. coli* such as W3110 (F⁻1⁻rph-1InV(rmD, rrnE)1 rph-1). In other embodiments, the engineered *E. coli* strain is a W3110 strain having a deletion of one or more of a pagP, lpxT, eptA, and 1pp polynucleotide. One exemplary and non-limiting 1pp polynucleotide is provided in GenBank Accession No. NC_07779, In still other embodiments, the engineered *E. coli* strain is a W3110 strain having a deletion of one or more of a pagP, lpxT, eptA, 1pp, and lpxM polynucleotides.

Accordingly, in some embodiments, an engineered *E. coli* strain is provided that comprises a plasmid containing one or more lipid modification polynucleotides selected from the group consisting of lpxE, lpxF, lpxO, lpxR, pagL, and pagP polynucleotides; an Lpp targeting polynucleotide; a linker polynucleotide; a transmembrane polynucleotide; and one or more peptide antigen encoding polynucleotides; wherein the *E. coli* strain has a deletion of a pagP, lpxT, eptA, and a 1pp polynucleotide. In one embodiment, an engineered *E. coli* strain is provided that comprises a plasmid containing one or more lipid modification polynucleotides selected from the group consisting of lpxE, lpxF, lpxO, lpxR, pagL, and pagP polynucleotides; an Lpp targeting polynucleotide; a linker polynucleotide; an ompA polynucleotide; a hemagglutinin polynucleotide, and/or a neuraminidase polynucleotide; wherein the *E. coli* strain has a deletion of a pagP, lpxT, eptA, and a 1pp polynucleotide.

As stated above, the antigen associated polynucleotides included herein can be peptide antigen encoding or polysaccharide antigen generating polynucleotides. Polysaccharide antigen generating polynucleotides include, but are not limited to, capsular antigen generating polynucleotides. Capsular antigen generating polynucleotides include, but are not limited to, O antigen generating polynucleotides and non-O antigen generating polynucleotides. Non-limiting examples of O antigens are those from *V. cholerae, S. typhimurium*, and *Shigella sonnei* and *flexneri* species. Non-limiting examples of non-O antigens are those from *Streptococcus pneumonia, Staphylococcus aureus*, and *Neisseria meningitidis*, Although not wanting to be bound by the following theory, it is believed that upon expression of the various lipid A moieties and the O antigen in the *E. coli*, the *E. coli* O antigen ligase WaaL covalently conjugates the synthesized *V. cholerae* O antigen to the lipid A core region of the modified *E. coli* lipid A. In a manner similar to the *V. cholerae* O antigen, the conserved O antigen genetic coding region of *Salmonella typhimurium* and *Shigella* spcs. are cloned and expressed in *E. coli* for covalent attachment to lipid A. Accordingly, in some embodiments, the engineered *E. coli* produces a lipid A moiety that is covalently attached to a polysaccharide antigen.

In some embodiments related to the expression of polysaccharide antigen generating polynucleotides, the engineered *E. coli* strain is a wild-type *E. coli* such as W3110 (F⁻1⁻rph-1InV(rmD, rrnE)1 rph-1). In other embodiments, the engineered *E. coli* strain is a W3110 strain having a deletion of one or more of a pagP, lpxT, eptA, and 1pp polynucleotide. One exemplary and non-limiting 1pp polynucleotide is provided in GenBank Accession No. NC_07779, Included herein are a homolog, ortholog, or paralog of the 1pp polynucleotide provided in GenBank Accession No. NC_07779, In still other embodiments, the engineered *E. coli* strain is a W3110 strain having a deletion of one or more of a pagP, lpxT, eptA, 1pp, and lpxM polynucleotides.

In some embodiments, an engineered *E. coli* strain is transformed with a vector containing one or more *V. cholerae* O antigen generating polynucleotides. This vector can be a pPM1001 plasmid. The *V. cholerae* O antigen generating polynucleotides include, but are not limited to, a wzm polynucleotide, a wzt polynucleotide, a wzx polynucleotide, a wzy polynucleotide, a rml polynucleotide, a galE polynucleotide, a wbeW polynucleotide, a wecC polynucleotide, a wecE polynucleotide, a wecB polynucleotide, a rfbT polynucleotide, a wbf region polynucleotide, and a homolog, ortholog or paralog thereof Further, *V. cholerae* O antigens include, but are not limited to, O antigens of the following serogroups: O1, O22, O139, and O140, In some embodiments, the *V. cholerae* O antigen is an O1 serogroup antigen selected from the group of an Inaba, Ogawa and Hikojima serotype. In some embodiments, the *V. cholerae* O antigen is an O1 serogroup antigen of the Inaba serotype. In some embodiments, the vector comprises one or more genes provided in GenBank Accession No. AE003852.1 (*Vibrio cholerae* O1 biovar El Tor str. N16961), or a homolog, ortholog or paralog thereof. In some embodiments, the vector comprises a polynucleotide having about 80%, about 85%, about 90%, about 95%, about 96%, about 97%, about 98%, or about 99% sequence identity with one or more genes provided in GenBank Accession No. AE003852.1.

Accordingly, in some embodiments, an engineered *E. coli* strain is provided that comprises a plasmid containing one or more lipid modification polynucleotides selected from the group consisting of lpxE, lpxF, lpxO, lpxR, pagL, and pagP polynucleotides; and one or more polysaccharide antigen generating polynucleotides; wherein the *E. coli* strain has a deletion of an rfbD polynucleotide and a 1pp polynucleotide. In other embodiments, an engineered *E. coli* strain is provided that comprises a plasmid containing one or more lipid modification polynucleotides selected from the group consisting of lpxE, lpxF, lpxO, lpxR, pagL, and pagP polynucleotides; and one or more polysaccharide antigen generating polynucleotides; wherein the *E. coli* strain has a deletion of a 1pp polynucleotide and a polynucleotide region spanning an rfbB polynucleotide to a wbbL polynucleotide. In other or further embodiments, an engineered *E. coli* strain is provided that comprises a plasmid containing one or more lipid modification polynucleotides selected from the group consisting of lpxE, lpxF, lpxO, lpxR, pagL, and pagP polynucleotides; and one or more *V. cholerae, S. enterica*, or *Shigella* spcs. O antigen generating polynucleotides; wherein the *E. coli* strain has a deletion of an rfbD polynucleotide and a 1pp polynucleotide.

In some embodiments, an engineered *E. coli* strain is transformed with a vector containing one or more *S. enterica* O antigen generating polynucleotides. In some embodiments, the O antigen is an *S. enterica enterica* subspecies antigen. In some embodiments, the vector comprises one or more genes provided in GenBank Accession No. AE006468 (*Salmonella enterica* subsp. *enterica serovar Typhimurium* str. LT2), or a homolog, ortholog or paralog thereof. In some embodiments, the vector comprises a polynucleotide having about 80%, about 85%, about 90%, about 95%, about 96%, about 97%, about 98%, or about 99% sequence identity with one or more genes provided in GenBank Accession No. AE006468, The *S. enterica* O antigen generating polynucleotides include, but are not limited to, a wzx polynucleotide, a wzy polynucleotide, a rml polynucleotide, a wba polynucleotide, a man polynucleotide, wda polynucleotide, a wcm polynucleotide, a wfb polynucleotide, a gmm polynucleotide, a wbd polynucleotide, a wbu polynucleotide, a wbe polynucleotide, a fcl polynucleotide, a wcl polynucleotide, a wej polynucleotide, a wdc polynucleotide, a wek polynucleotide, a qdt polynucleotide, a gmd polynucleotide, an fdt polynucleotide, a wcn polynucleotide, a wdc polynucleotide, a wpb polynucleotide, a wei polynucleotide, a gna polynucleotide, a gne polynucleotide, a wbb polynucleotide, a rfbA polyulceotide, a rfbB polynucleotide, a rfbD polynucleotide, a rfbF polynucleotide, a rfbG polynucleotide, a rfbK polynucloeitde, a rfbM polynucleotide, a rfbP polynucleotide, and a homolog, ortholog or paralog thereof.

In some embodiments, an engineered *E. coli* strain is transformed with a vector containing one or more *Shigella sonnei* and/or *Shigella flexneri* O antigen generating polynucleotides. The *S. sonnei* O antigen generating polynucleotides include, but are not limited to, a wzz polynucleotide, a wbgT polynucleotide, a wbgU polynucleotide, a wzx polynucleotide, a wzy polynucleotide, an IS630 polynucleotide, a wbgV polynucleotide, a wbgW polynucleotide, a wbgX polynucleotide, a wbgY polynucleotide, a wbgZ polynucleotde and an aqpZ' polynucleotide. In some embodiments, the vector comprises one or more genes provided in GenBank Accession No. CP001383.1 (*Shigella flexneri* 2002017), or a homolog, ortholog, or paralog thereof. In some embodiments, the vector comprises a polynucleotide having about 80%, about 85%, about 90%, about 95%, about 96%, about 97%, about 98%, or about 99% sequence identity with one or more genes provided in GenBank Accession No. CP001383.1, In other or further embodiments, the vector comprises one or more genes provided in GenBank Accession No. AE005674.2 (*Shigella flexneri* 2a str. 301) or a homolog, ortholog, or paralog thereof. In some embodiments, the vector comprises a polynucleotide having about 80%, about 85%, about 90%, about 95%, about 96%, about 97%, about 98%, or about 99% sequence identity with one or more genes provided in GenBank Accession No. AE005674.2, The *S. flexneri* O antigen generating polynucleotides include, but are not limited to, a wzx polynucleotide, a wzy polynucleotide, an rml polynucleotide, a wbu polynucleotide, a gnd polynucleotode, a galF polynucleotide, a wfd polynucleotide, a glf polynucleotide, a wbd polynucleotide, a man polynucleotide, a wba polynucleotide, a psb polynucleotide, a wbg polynucleotide, a wbs polynucleotide, a wbw polynucleotide, a fnl polynucleotide, a qnl polynucleotide, a wfe polynucleotide, a wfa polynucleotide, a wbb polynucleotide, and a wff polynucleotide.

In still other embodiments, an engineered *E. coli* strain is provided that comprises a vector containing one or more lipid modification polynucleotides selected from the group consisting of lpxE, lpxF, lpxO, lpxR, pagL, and pagP polynucleotides; and one or more *Streptococcus pneumoniae, Staphylococcus aureus*, or *Neisseria meningitidis* capsular antigen generating polynucleotides (non-O antigen); wherein the *E. coli* strain has a deletion of an rfbD polynucleotide. In some embodiments, the vector comprises one or more genes provided in GenBank Accession No AE005672.3 (*Streptococcus pneumoniae* TIGR4 or a homolog, ortholog or paralog thereof. The *S. pneumoniae* capsular (non-O) antigen generating polynucleotides include, but are not limited to, a wzg polynucleotide, a wzh polynucleotide, a wzd polynucleotide, a wze polynucleotide, a wch polynucleotide, a wci polynucleotide, a wzy polyncueltodie, a wzx polynucleotide, and a rml polynucleotide. In other or further embodiments, the vector comprises one or more genes provided in GenBank Accession No. CP000255.1 (*Staphylococcus aureus* subsp. *aureus* USA300_FPR3757) or a homolog, ortholog or paralog thereof. The *S. aureus* capsular (non-O) antigen generating polynucleotides include, but are not limited to, a cap1A polynucleotide, a cap1B polynucleotide, a cap1C polynucleotide, a cap 1D polynucleotide, a cap1E polynucleotide, a cap1F polynucleotide, cap1G polynucleotide, cap1H polynucleotide, cap1I polynucleotide, cap1J polynucleotide, cap1K polynucleotide, cap1L polynucleotide, cap1M polynucleotide, cap1N polynucleotide, and cap1O polynucleotide. The *N. meningitides* capsular (non-O) antigen generating polynucleotides include, but are not limited to, a myn polynucleotide, a sia polynucleotide, a lip polynucleotide, and an mtr polynucleotide.

The compositions and methods described herein advantageously provide a means for producing a whole vaccine (an antigen and an adjuvant) from a bacterium. The compositions and methods further provide a broad range of lipid A moiety and antigen combinations, and thereby allows for selection and creation of lipid A and antigen combinations that are specifically tailored to generate a desired immune response. Accordingly, the compositions produced by the *E. coli* strains are highly useful as vaccines or vaccine components.

Therefore, included herein is a composition isolated from an engineered *E. coli* strain as described above or below, wherein the composition comprises one or more lipid A moieties linked to one or more antigens. In some embodiments, the one or more lipid A moieties are covalently attached to one or more polysaccharide antigens in the composition. In other or further embodiments, the one or more lipid A moieties are co-localized with the one or more peptide antigens at the outer membrane of an *E. coli* cell or an outer membrane vesicle in the composition.

Also included herein is a pharmaceutical composition comprising one or more lipid A moieties linked to one or more antigens isolated from an engineered *E. coli* strain as described above or below. The pharmaceutical compositions include a therapeutically effective amount of the isolated lipid A-antigen compounds described herein in combination with a pharmaceutically acceptable carrier and, in addition, can include other medicinal agents, pharmaceutical agents, carriers, or diluents.

As used herein, the term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences*, 21st Edition, ed. University of the Sciences in Philadelphia, Lippincott, Williams & Wilkins, Philadelphia Pa., 2005, Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.). To provide for the administration of such dosages for the desired therapeutic treatment, compositions disclosed herein can advantageously comprise between about 0.1% and 99% by weight of the total of one or more of the lipid A-antigen compounds based on the weight of the total composition including carrier or diluent.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A-C. The gene and protein sequences of HA2 and a timeline of mouse vaccinations studies. (A) The HA2 domain from Influenza A H1N1 PR/8/1934 (SEQ ID NOs: 13-14; Bommakanti et al., 2012) and (B) H3N2 HongKong/68 (SEQ ID NOs: 15-16; Bommakanti et al., 2010) that are used in the influenza vaccines. The genetic coding sequences and the translated amino acid sequence of each are included. (C) Mice are vaccinated with orally with Lpp-OmpA-HA expressing whole bacteria or isolated OMVs. Primary vaccination occurs on day 0 and mice are boost vaccinated on day 28, On day 44 mice are challenged with influenza virus and monitored for illness. On day 7 post infection, mice are sacrificed for serum and lung collection.

FIGS. 5A-E. Phenotypic changes after lethal challenge. (A) Mice (n=5) were vaccinated intranasally with OMVs and challenged with a lethal dose of influenza. Changes in weight were monitored and reported as fractional weight for each group. (B) PBS-vaccinated mouse on day seven post-challenge (C) MPL-vaccinated mouse on day seven post infection (D) MPL-HA-vaccinated mice on day seven post-infection (E) Inactivated virus vaccinated mouse on day seven post-infection.

DESCRIPTION OF ILLUSTRATIVE EMBODIMENTS

Figure 1:
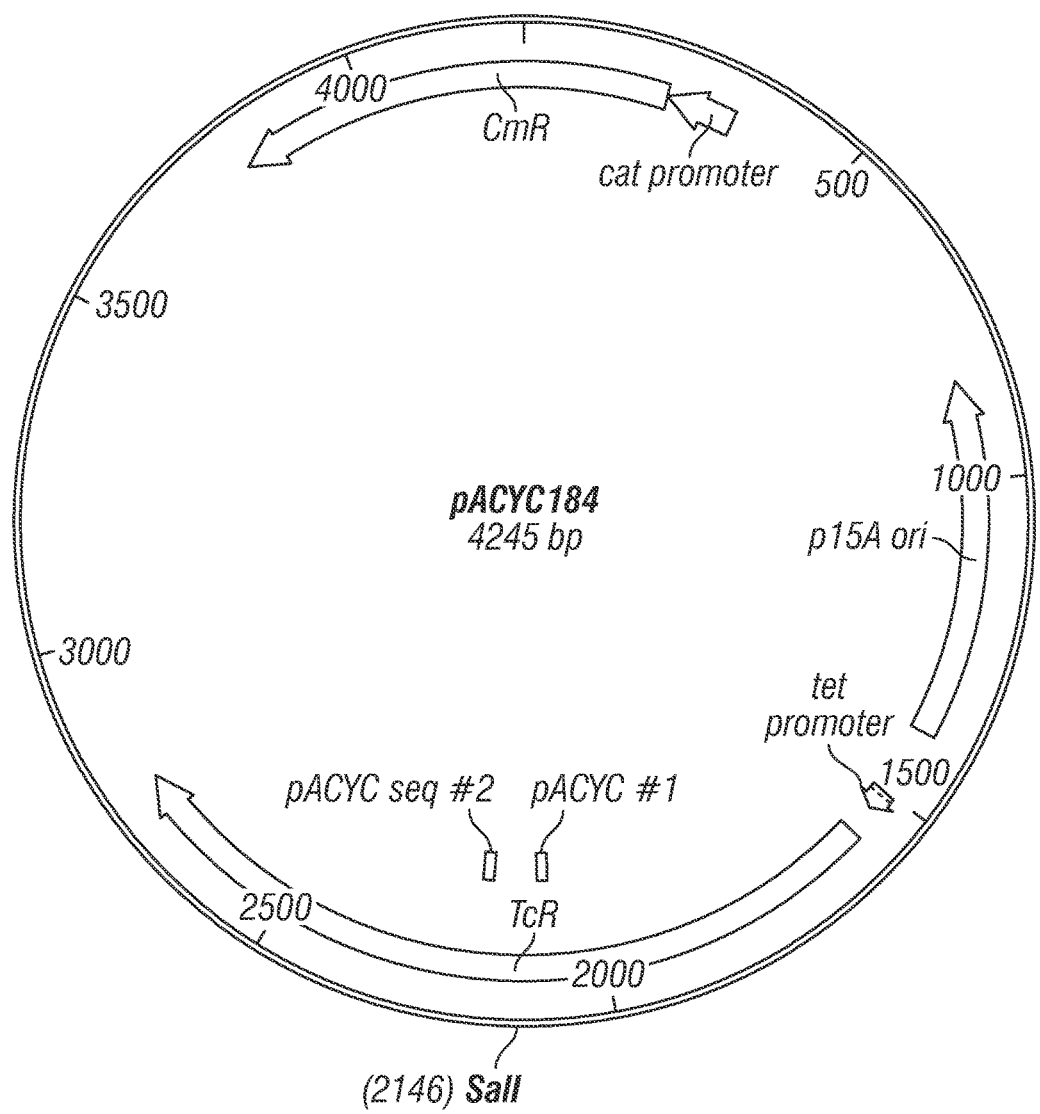
FIG. 1. A schematic representation of the pACYC184 plasmid.

Provided herein are engineered *Escherichia coli* strains that create lipid A moieties linked with antigen and methods for producing these *E. coli* strains. In some embodiments, the lipid A moiety is covalently linked to the antigen. In other embodiments, the lipid A moiety is linked to the antigen via a co-localization in an outer membrane of the *E. coli*. The compositions and methods described herein advantageously provide a means for producing a whole vaccine (a linked antigen and an adjuvant) from a bacterium. The compositions and methods further provide a broad range of possible lipid A moiety and antigen combinations, and thereby allows for selection and creation of lipid A and antigen combinations that are specifically tailored to generate a desired immune response. Accordingly, the compositions created by the *E. coli* strains are highly useful as vaccines or vaccine components.

Provided herein are new bacterial vaccine production platforms where nonpathogenic bacteria produce antigen and adjuvant on the cell surface or where the adjuvant and antigen are purified from whole bacteria using OMVs. Previously, a bacterial system was developed in nonpathogenic *E. coli* that expressed lipid A modification genes from a plasmid. This work resulted in 61 distinct *E. coli* strains that each generated a unique lipid A adjuvant molecule on the surface of the cell (Needham et al., 2013). In this work, this new adjuvant technology is built on by adapting both protein and carbohydrate antigens to express coordinately with a bacterial-derived lipid adjuvant on the cell surface. Initial pilot vaccines were produced with a HA2-domain protein that was tested in mice to understand the efficacy of this system. The influenza vaccine successfully induced an antibody response specific to the HA protein, resulted in reduced viral titers after lethal challenge, and protected vaccinated mice from influenza. In addition, this vaccine platform has also been engineered to directly link carbohydrate antigens onto a lipid adjuvant, such as MPL, to produce glycoconjugate vaccines. Carbohydrate antigens and lipid adjuvants are produced on the cell surface and purified as a vaccine to protect from cholera infections.

I. Definitions

As used in the specification and claims, the singular form "a," "an," and "the" include plural references unless the context clearly dictates otherwise. For example, the term "a cell" includes a plurality of cells, including mixtures thereof.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. DNA for a presequence or secretory leader may be operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

The term "deletion," when referring to a polynucleotide sequence or a gene, is used herein to refer to an effective deletion of the function of the polynucleotide sequence or gene. More specifically, a deletion includes a complete removal, a partial removal, and one or more mutations that render the polynucleotide sequence, the gene, or a polypeptide encoded by the polypeptide or gene, inactive or ineffective for its desired purpose.

As used herein, "expression" refers to the process by which polynucleotides are transcribed into mRNA and/or the process by which the transcribed mRNA is subsequently being translated into peptides, polypeptides, or proteins.

A "gene" refers to a polynucleotide containing at least one open reading frame that is capable of encoding a particular polypeptide or protein after being transcribed and translated.

The terms "link," "linked," and "linkage" refer to a close proximity and do not require a physical touching. In some embodiments, these terms refer to a covalent bond. In other embodiments, these terms refer to a co-localization such as at an outer membrane.

A "pharmaceutical composition" is intended to include the combination of an active agent with a pharmaceutically acceptable carrier, inert or active, making the composition suitable for diagnostic or therapeutic use in vivo or ex vivo.

The term "pharmaceutically acceptable carrier" means a carrier or excipient that is useful in preparing a pharmaceutical composition that is generally safe and non-toxic, and includes a carrier that is acceptable for veterinary and/or human pharmaceutical use. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below. The pharmaceutical compositions also can include preservatives. A "pharmaceutically acceptable carrier" as used in the specification and claims includes both one and more than one such carrier.

The terms "polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also refers to both double- and single-stranded molecules.

A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

As used herein, an "antigen associated polynucleotide" includes a polynucleotide that encodes the antigen polypeptide and a polynucleotide that encodes a polypeptide, which polypeptide functions to create or modify the antigen. In some embodiments, an antigen associated polynucleotide encodes an enzyme that creates or modifies a polysaccharide antigen such as a capsular antigen. Capsular antigens include O antigens and non-O antigens. These antigen associated polynucleotides are referred to herein as "polysaccharide generating."

The term "polypeptide" is used in its broadest sense to refer to a compound of two or more subunit amino acids, amino acid analogs, or peptidomimetics. A peptide of three or more amino acids is commonly called an oligopeptide if the peptide chain is short. If the peptide chain is long, the peptide is commonly called a polypeptide or a protein.

A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1, Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Transformation" of a cellular organism with DNA means introducing DNA into an organism so that at least a portion of the DNA is replicable, either as an extrachromosomal element or by chromosomal integration.

The term "vector" means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may in some instances, integrate into the genome itself. A plasmid is the most commonly used form of vector, however, the invention is intended to include such other forms of vectors which serve equivalent function as and which are, or become, known in the art.

II. Aspects of the Present Embodiments

Influenza virus is a highly transmissible respiratory pathogen that results in about 40,000 deaths annually and kills millions during pandemic years (Fan et al., 2004). Influenza viruses are classified into two epidemiologically interesting types including A and B. While only one serologically distinct influenza B virus exists, influenza A viruses are highly variable and strains are subtyped based on two antigenic surface glycoproteins called hemagglutinin (HA) and neuraminidase (Lamb and Krug, 2001). While influenza A viruses include 16 different HA proteins (H1-H16) and nine neuraminidase (N1-N9), Human-infectious influenza viruses are primarily A-type H1N1, H2N2, H3N2, and B-type viruses, but cross-species infections from avian-associated H5N1 and H7N7, and H9N2 and swine-associated strains have recently emerged. These avian influenza outbreaks are extremely worrisome because of close human interaction with birds present the possibility of a new influenza pandemic (Horimoto and Kawaoka, 2005).

Currently, vaccination is considered the most effective way to prevent influenza transmission. The most common influenza vaccine consists of heat-inactivated H1N1, H3N2, and B-type viruses that are grown in chicken eggs, but recently, a cold-adapted live virus has been developed that actively replicates in the nasal passages to generate immunity. While each of these vaccination methods produce protective antibodies to protect from influenza, each has drawbacks. Due to antigenic drift and shift of the A-type viruses, influenza vaccines require regular modifications based on emergent viral strains. However, production of each virus strain takes at least six months. Therefore, quick production of vaccines in epidemics/pandemics is not possible with current technology. Furthermore, a recombinant vaccine that can be produced in a timeframe of days or weeks that offers long-term protection from influenza would be ideal for controlling viral outbreaks.

Influenza HA is a highly immunogenic protein that coats the surface of the virus and it has been the target of many vaccines (Cox, 2005). HA is required for influenza infection by promoting fusion with host cells. Cellular proteases cleave the HA protein into HA1 and HA2 domains, which comprise a necessary step for viral infection (Skehel and Wiley, 2000). Viral entry is mediated by the HA1 domain binding to salic acid receptors on the surface of the host cell. Through endocytosis the virion enters the cell where it is transported to the endosome where the acidic pH promotes structural changes in the HA protein. Conformational shifts expose the HA2 domain, and promote fusion of the viral and endosomal membranes. The crystal structures of HA have revealed that cleavage of the HA1 and HA2 domains and the low pH of the endosome are required for structural alterations that promote viral infection (Chen et al., 1998; Bullough et al., 1994; Sauter et al., 1992).

While the HA2 domain of HA is considerably more conserved than the HA1 domain, neutralizing antibodies directed at both protein domains offer protection from influenza challenge (Skehel and Wiley, 2000; Gocnik et al., 2008; Smirnov et al., 2000; Okuno et al., 1994). In fact, several neutralizing antibodies has been isolated that target the conserved HA2 domain. These antibodies target conserved epitopes in the HA2 protein of several influenza A subtypes to offer broad protection (Ekiert et al., 2009; Sui et al., 2009; Throsby et al., 2008; Okuno et al., 1993; Sancheck-Fauquier et al., 1987). Mechanistically, the antibodies presumably inhibit the conformational changes that are necessary for viral and host membrane fusion at low pH. Blocking viral entry by targeting the conserved HA domain could offer widespread protection from influenza viruses in human, chickens, and swine, which are the major reservoirs for these viruses.

A bacterial-based vaccine was engineered that targets the conserved domain of HA2 to offer widespread protection against influenza A viruses. A mouse model was used to demonstrate the efficacy of the influenza protein-based vaccine. The benefits of this new technology are that it is a quick, low cost, high yield production of influenza vaccines that does not require growth of viruses in chicken eggs. Incorporating a conserved antigenic HA2 epitope into a bacterial based vaccine system could be valuable against the threat of epidemics/pandemics.

In addition to this protein-based vaccine, this system has also been adapted to produce glycoconjugate vaccines that target carbohydrate epitopes of pathogenic bacteria. The efficacy of this system has been demonstrated by generating a vaccine against the conserved O-antigen of *Vibrio cholerae*, Cholera disease is a potentially lethal diarrheal disease that affects millions of people every year (Harris et al., 2012; Kaper et al., 1995). The well-conserved Vibrio cholerae O-antigen has been shown to provide a protective immune response against infection (Seed et al., 2012). Therefore, a bacterium was engineered to produce the *V. cholerae* O-antigen as the antigen in the bacterial-based vaccine system.

III. Nucleic Acid-Based Expression Systems

A wide range of nucleic acid-based expression systems may be used for the expression of polypeptide antigens or genes controlling synthesis of polysaccharide antigens of the embodiments. For example, one embodiment of the invention involves transformation of bacteria with the coding sequences of fusion polypeptides comprising a polypeptide antigen linked to a membrane anchor sequence (and section signal). Numerous expression systems exist that comprise some or all of the sequence components discussed below.

The term "expression vector" refers to a vector containing a nucleic acid sequence coding for at least part of a gene product capable of being transcribed and then translated into a polypeptide. Expression vectors can contain a variety of "control sequences," which refer to nucleic acid sequences necessary for the transcription and possibly translation of an operably linked coding sequence in a particular host organism (e.g., gram positive or gram negative bacteria). In addition to control sequences that govern transcription and translation, vectors and expression vectors may contain nucleic acid sequences that serve other functions as well and are described infra.

1, Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

Preferably a promoter a promoter for use according to the embodiments is a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. Furthermore, it is contemplated that the control sequences that direct transcription and/or expression of sequences within non-nuclear organelles such as mitochondria, chloroplasts, and the like, can be employed as well.

In preferred aspects, a promoter (or promoter enhancer system) for use according to the embodiments is an inducible promoter that provides expression of a sequence based on an external stimulus. For example, the inducible promoter may be a promoter that provides expression only in the presence of a particular compound (e.g., IPTG), at a particular pH, or in specific environmental (e.g., lighting) conditions.

2, Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3, Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4, Termination Signals

The vectors or constructs prepared in accordance with the present invention will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels.

Terminators contemplated for use in the invention include any known terminator of transcription described herein or known to one of ordinary skill in the art, including but not limited to, for example, rhp dependent or rho independent terminators. In certain embodiments, the termination signal may be a lack of transcribable or translatable sequence, such as due to a sequence truncation.

5, Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

6, Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker, such an antibiotic resistance marker.

7, Fusion Polypeptides

As described above, in some aspects a vector of the embodiments comprises a sequence for expression, which comprises a fusion of a membrane anchor sequence and an antigen polypeptide. Furthermore, in some aspects, the fusion polypeptide comprises a secretion signal that directs the fusion protein to the bacterial (outer) membrane. Optionally, the fusion polypeptide further comprises a linker positions between the antigen polypeptide sequence and the membrane anchor sequence.

a. Signal Sequences

In some aspects, a fusion polypeptide of the embodiments comprises a signal sequence that targets the fusion polypeptide to the membrane (and may be cleaved away from the fusion). In certain aspects, the signal sequence can be from a gram negative bacteria (e.g., E. coli). For example, the signal sequence can be from Lpp. In further aspects, the signal sequence can be a signal sequence from an autotransporter polypeptide of a gram negative bacteria. For example, the signal sequence can be from AIDA-I, EstA, MisL, Hbp, Ag43, BrkA, OmpA, OmpC, OmpX, LamB, FhuA, PfaI, EspP, IgAP, Pet or YfaI (see, e.g., Nicolay et al., 2015 and van Bloois et al., 2011, each incorporated herein by reference).

b. Membrane Anchor Sequence

Certain aspect of the embodiments concern fusion polypeptides that comprise a bacterial membrane anchor sequence. For example, the membrane anchor sequence can be composed of all or part of an integral membrane protein from a gram negative bacteria. In further aspects, the membrane anchor sequence can be a non-integral membrane polypeptide, such as a lipoprotein or a component of a bacterial surface appendage. In particular aspects, the bacterial membrane anchor sequence can be an outer membrane anchor sequence. In some aspects, the sequence can be a beta-barrel domain from an autotransporter polypeptide of a gram negative bacteria. For example, the membrane anchor sequence can comprise a membrane anchor domain from AIDA-I, EstA, MisL, Hbp, Ag43, BrkA, OmpA, OmpC, OmpX, LamB, FhuA, PfaI, EspP, IgAP, Pet, YfaI or MraY (see, e.g., Nicolay et al., 2015 and van Bloois et al., 2011, each incorporated herein by reference). In further aspects, the bacterial membrane anchor sequence comprises the membrane anchor sequence from OmpA.

c. Linker Sequence

It will be understood that in certain cases, a fusion polypeptide may comprise additional amino acids positioned between the antigen polypeptide sequence and the membrane anchor sequence. In general these sequences are interchangeably termed "linker sequences" or "linker regions." One of skill in the art will recognize that linker regions may be one or more amino acids in length and often comprise one or more glycine residue(s) which confer flexibility to the linker. A variety of linkers can be used as part of fusion polypeptide of the embodiments. In preferred aspects, the optional linker sequence is positioned between the membrane anchor sequence and the antigen polypeptide sequence. In certain aspects the linker sequence comprises at least or about 1, 2, 3, 4, 5, 6, 7, 8, 9, 10, 11, 12, 13, 14, 15, 16, 17, 18, 19 or 20 amino acids. In still further aspects the linker comprises between about 10 and 200, 10 and 100, 20 and 100, 40 and 100 or 50 and 90 amino acids. In certain aspects, the linker sequence may comprise two, three, four or more Gly positions or a poly Gly sequence having two or more consecutive Gly positions.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Bacterial strains and growth. For all experiments, *E. coli* strains were initially grown from freezer stocks on LB agar overnight at 37° C. After initial growth, isolated colonies were inoculated into 10 ml cultures and incubated overnight at 37° C. for use in experiments. Ampicillin was used at 100 μ/ml, while chloramphenicol was used at 15 μ/ml for all experiments. IPTG was used at a concentration of 100 μM.

Immunoblot analysis. To detect 6x-his tagged proteins, *E. coli* preparations were grown and diluted to OD600 of 1.0 for whole cell lysates. 5 μof total protein from whole bacterial cells or isolated OMVs was separated by SDS-PAGE and transferred onto nitrocellulose Immunoblotting was performed with mouse-anti-5x-his antibody (Qiagen) at a dilution of 1:2000 or anti-*Vibrio* antibody at a dilution of 1:40,000 (KPL-seracare). Anti-mouse or anti-rabbit conjugated-HRP secondary antibody (GE Healthcare) or was used at a concentration of 1:10,000, respectively. Detection was performed using Pierce® ECL Western Blotting Substrate (Thermo Scientific).

Fluorescent analysis. *E. coli* cells were examined as previously described with some modifications (Lam et al., 1994). In brief, cells were grown to mid log phase OD600 of 0.5 and 1 ml was fixed in 4% paraformaldehyde for 20 minutes at 25° C. Samples were washed twice with 2 ml of PBS and then incubated in 10% BSA resuspended in PBS for 20 minutes. Cells were resuspended in 10% BSA-PBS with a 1:100 dilution of mouse-anti-5x-his antibody (Qiagen) or anti-*Vibrio* antibody (KPL-seracare) and incubated at 25° C. for 1 h. Samples were washed three times in PBS and a fluorescein-conjugated anti-mouse or an anti-rabbit secondary antibody was diluted 1:200 in 10% BSA-PBS and incubated at 25° C. for 1 h. The cells were washed four times with PBS. 10 μl of cells were mounted on glass slides under a coverslip and examined on a Nikon Eclipse 80i microscope.

Mass spectrometry. For mass spectrometry, lipid A was analyzed using a MALDI-TOF/TOF (ABI 4700 Proteomics Analyzer) mass spectrometer in the negative mode as previously described (Hankins et al., 2011).

Immunization and challenge studies. Female Balb/C mice were immunized orally with $1 \times 10^8$ bacterial cfu or intranasal administration with OMVs containing 20 μg of total protein. All bacterial strains were expression enzymes from the pELOP plasmid (Needham et al., 2013) to generate MPL. All animals were boosted four weeks later with equivalent amounts. At week six, the mice were challenged with $35 \times LD_{50}$ of A/PR/8/1934 (H1N1). At day seven, five mice from each group were sacrificed for lung viral titers, while the rest were monitored for seventeen days. Serum was collected two weeks after the last vaccination for antibody analysis.

Lung viral titers. A confluent layer of MDCK cells was washed with PBS and lung homogenate was added at 1:10, 1:100, 1:1000 etc. dilutions. Cells were incubated at 33° C. for 1 h with shaking every 15 minutes to ensure an equal distribution of virus throughout the plate. After 1 h the media was removed and the cells were overlayed with 25 ml of 2% DMEM containing 2% penicillin/streptomycin, 2.5 μg/ml of NAT, and 2% agarose. Solidified plates were inverted and incubated at 33° C. for three days. Plaques were reported as viral forming units/lung. All titers were performed in triplicate and averaged.

ELISAs. For antibody analysis, 3 μg of recombinant soluble HA2 was purified and immobilized on a 96-well plate. Wells were probed with serial dilutions of mouse serum diluted in PBS. After washing, anti-mouse conjugated-HRP secondary antibody (GE Healthcare) was used at a concentration of 1:10,000, Detection was performed using Pierce® ECL Western Blotting Substrate (Thermo Scientific). The absorbance was read at 405 nm.

Example 1

Plasmids and *E. coli* Strains for the Preparation of Lipid A/Polysaccharide Antigen Vaccines Six genes, lpxE, lpxF, lpxO, lpxR, pagL, and pagP, were cloned individually into pQLinkN and expressed in wild-type *E. coli* for co-expression as described in U.S. Patent Application Publication No. 2013/0230555, which is hereby incorporated by reference in its entirety. The six genes originated from the following species: pagP from *E. coli*; pagL, lpxR, and lpxO from *Salmonella enterica* serovar *Typhimurium*; and lpxE and lpxF from *Francisella tularensis*, Specifically, the primers listed below in Table 1 were used for said cloning.

TABLE 1

| | Primer sequences | |
|---|---|---|
| LpxEBamHIfor | 5'-GCGGATCCATGCTC AAACAGACATTA-3' | SEQ ID NO: 1 |
| LpxEBamHIrev | 5'-GCGCGGCCGCCTAA ATAATCTCTCTATT-3' | SEQ ID NO: 2 |
| LpxFBamHIfor | 5'-GCGGATCCTTGGCA AGATTTCATATC-3' | SEQ ID NO: 3 |
| LpxFBamHIrev | 5'-GCGCGGCCGCTCAA TATTCTTTTTTACG-3' | SEQ ID NO: 4 |
| PagLBamHIfor | 5'-GCGGATCCATGTAT ATGAAGAGAATA-3' | SEQ ID NO: 5 |
| PagLBamHIrev | 5'-GCGCGGCCGCTCAG AAATTATAACTAAT-3' | SEQ ID NO: 6 |
| LpxOEcoRIfor | 5'-GCGAATTCATGTTC GCAGCAATCATT-3' | SEQ ID NO: 7 |
| LpxOBamHIrev | 5'-GCGGATCCTCAGAG GAGGCTGAAAAG-3' | SEQ ID NO: 8 |

TABLE 1-continued

Primer sequences

| | | |
|---|---|---|
| PagPBamHIfor | 5'-GCGGATCCATGAAC GTGAGTAAATAT-3' | SEQ ID NO: 9 |
| PagPNotIrev | 5'-GCGCGGCCGCTCAA AACTGAAAGCGCAT-3' | SEQ ID NO: 10 |
| LpxRBamHIfor | 5'-GCGGATCCATGAAC AAATACAGCTAT-3' | SEQ ID NO: 11 |
| LpxRNotIrev | 5'-GCGCGGCCGCTCAG AAGAAGAAGGTGAT-3' | SEQ ID NO: 12 |

Transformation of wild-type *E. coli* with pQlinkN-derived plasmids that contained various combinations of the lpxE, lpxF, lpxO, lpxR, pagL, and pagP genes yielded *E. coli* strains that produce diverse lipid A species. The lipid A species are described in U.S. Patent Application Publication No. 2013/0230555, However, for *E. coli* expression of linked lipid A/polysaccharide antigen compositions, the lipid A modification genes (lpxE, lpxF, lpxO, lpxR, pagL, and pagP) and their IPTG inducible promoters were transferred to a pACYC184 plasmid and two plasmids were employed. First, the lipid A modification genes (lpxE, lpxF, lpxO, lpxR, pagL, and pagP) and their promoters were amplified from the pQlinkN-derived plasmid with engineered SalI sites and the digested fragments were cloned into SalI-digested pACYC184, which contains a p15A replicon. A schematic of the pACYC184 plasmid is provided in FIG. 1.

Figure 6A:
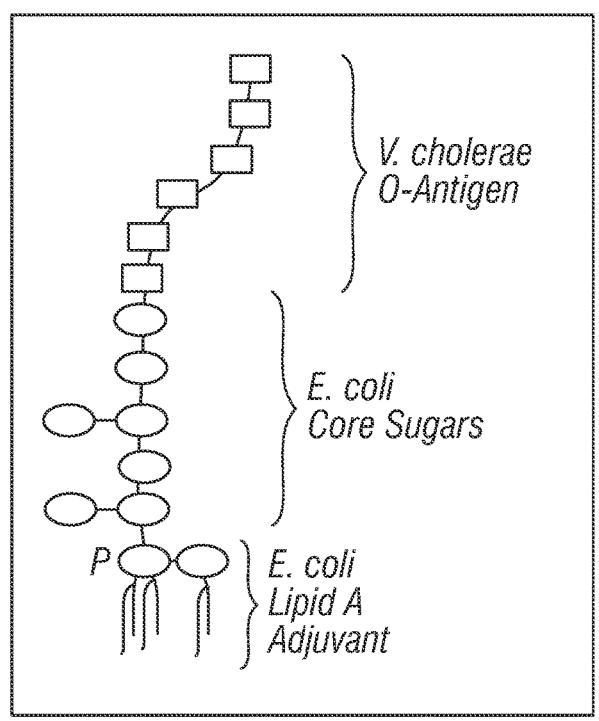
FIGS. 6A-D. Engineering a glycoconjugate-based antigen/adjuvant vaccine delivery platform. (A) An illustration of a *V. cholerae* O -antigen linked to *E. coli* lipooligosaccharide. *E. coli* MPL is attached to core oligosaccharide that gets covalently linked to the O-antigen of *V. cholerae*, (B) Pro-Q® emerald 300 stain of lipopolysaccharide from *V. cholerae*, *E. coli* DH1, BN1 expressing pPM1001, and BN1 with a mutation in the rfbD gene expressing pPM1001, (C) BN1 cells that were exposed to a FITC-labeled secondary antibody specific to the *V. cholerae* O -antigen. (D) MALDI-TOF mass spectrometry analysis of lipid A isolated from cells expressing the enzymes to make MPL.
Figure 6B:
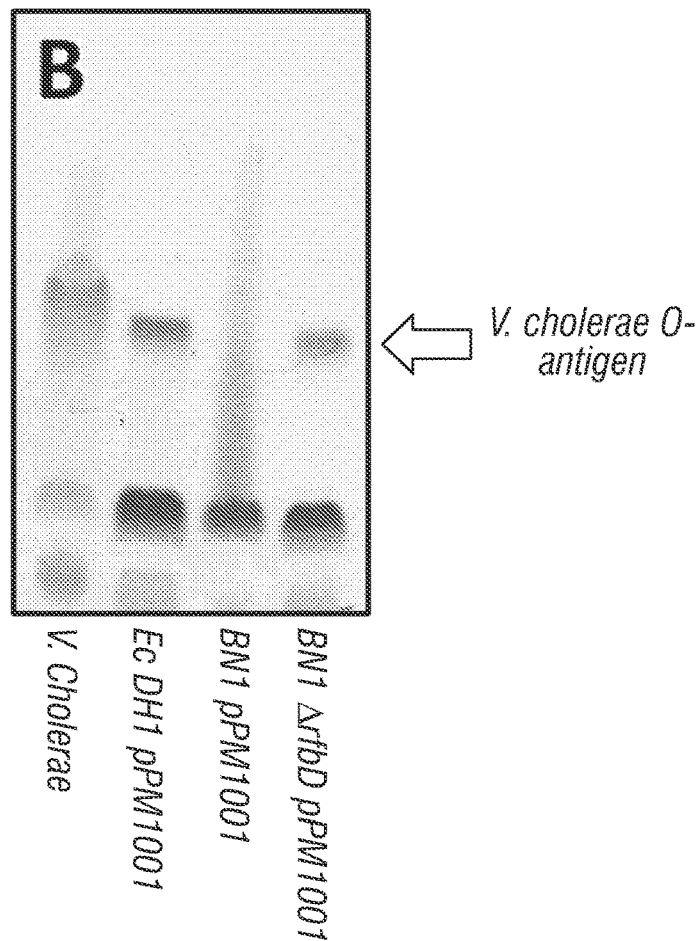
Figure 6C:
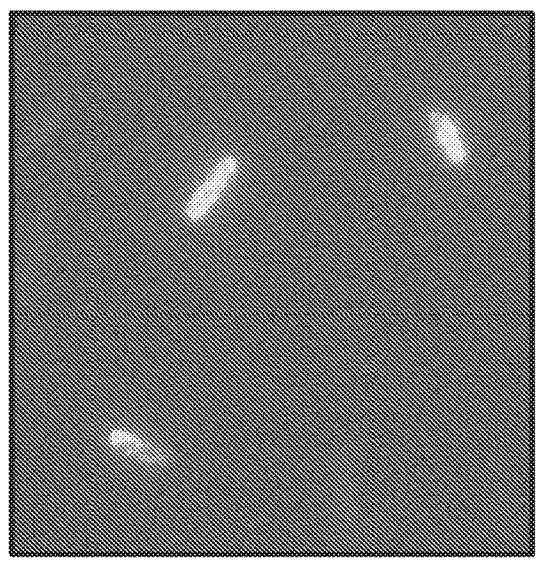
Figure 6D:
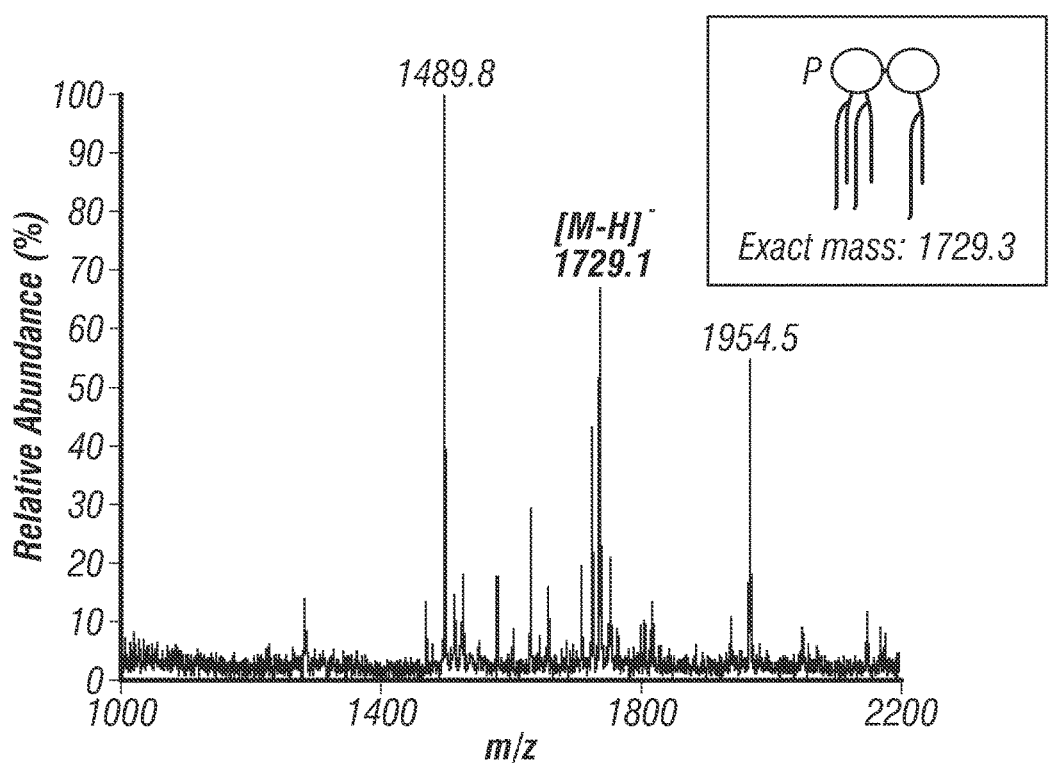
Figure 7:
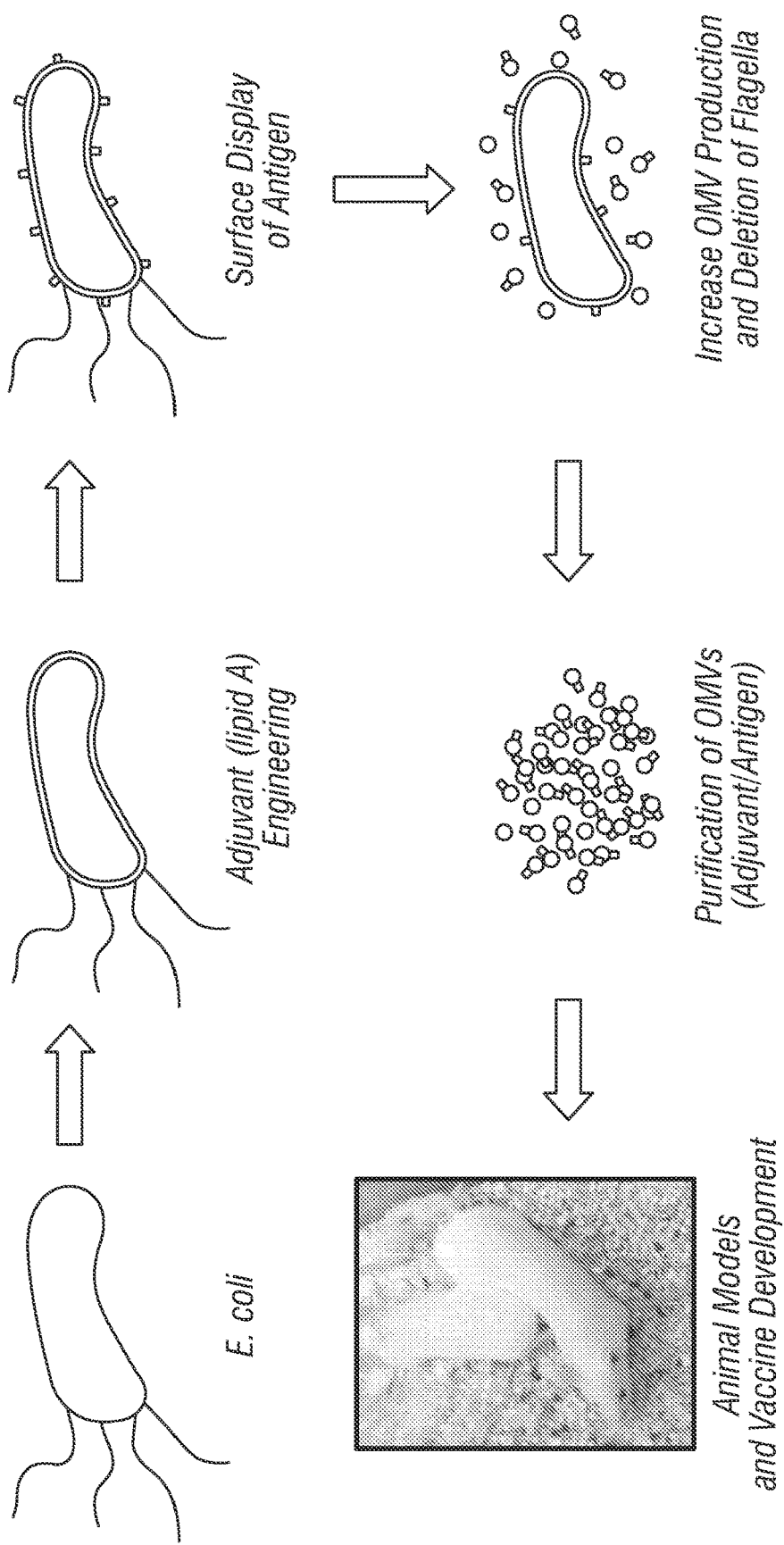
FIG. 7. Outline of the combinatorial platform for the display of surface adjuvants and antigens in *E. coli*.

Next, a plasmid, pPM1001, was obtained from Monash University that contains the genes required to synthesize the O1 O-antigen from Vibrio cholerae (Manning et al., 1986). More specifically, the plasmid contained one or more of: gmhD gene, a manC gene, a manB gene, a gmd gene, a wbeE gene, a wbeG gene, a wzm gene (ABC transport), a wzt gene (ABC transport), a wbeK gene, a wbeL gene, a wbeM gene, a wbeN gene, a wbeO gene, a wbeP gene, a wbeT gene, a wbeU gene, a wbeV gene, a gale gene, and a wbeW gene, and a wbf region gene. For optimal expression of O antigen genes in *E. coli*, either the rfbD gene (Eck2034; see, for example, GenBank Accession No. NC_007779) or the entire *E. coli* O antigen biosynthetic genetic region from ribB to wbbL (Eck2025-Eck2035) were chromosomally deleted by P1 vir phage transduction using Keio mutants or lambda red recombination, respectively (Baba et al., 2006; Touze et al., 2008). *E. coli* manifesting one of these deletions were then transformed with the plasmid pPM1001 and a pACYC184 plasmid selected from the group of plasmids containing the various combinations of the lpxE, lpxF, lpxO, lpxR, pagL, and pagP genes.

All *Escherichia coli* W3110 strains were grown from freezer stock on Luria-Bertani Broth (LB) or 2× Nutrient broth with 5 g/L of NaCl at 25° C., 30° C., or 37° C. and supplemented with 100 mg/mL ampicillin, 15 mg/mL chloramphenicol, or 30 mg/mL kanamycin when appropriate. When required, 50 μM-1mM isopropyl β-D-1-thiogalactopyranoside (IPTG) was added as determined by TLC analysis of lipid A enzyme activity. To increase production of outer membrane vesicles (OMVs), the gene Eck1673, which encodes the major outer membrane lipoprotein Lpp, was deleted from the *E. coli* genome. The Eck1673 gene is also known as lpp. One exemplary lpp polynucleotide is provided in GenBank Accession No. NC_007779, Deletion of the Lpp lipoprotein resulted in a 100- to 1000-fold increased production of OMVs in *E. coli* strains.

It is believed that upon expression of the various lipid A species and the O antigen in the *E. coli*, the *E. coli* O antigen ligase WaaL covalently conjugated the synthesized *V. cholerae* O antigen to the lipid A core region of the modified lipid A adjuvant. In a manner similar to the *V. cholerae* O antigen, the conserved O antigen genetic coding region of *Salmonella typhimurium* and *Shigella* spcs. are cloned and expressed in *E. coli* for covalent attachment to lipid A. In addition, capsule biosynthesis genetic coding regions from *Streptococcus pneumoniae* and *Staphylococcus aureus* including, but not limited to, a wzm gene (ABC transport), a wzt gene (ABC transport), a wzx gene (flippase) and/or a wzy gene (polymerase), are cloned in a similar manner and ligated to engineered *E. coli* lipid A molecules.

The above-described glycolipids were then isolated in outer membrane vesicles, or OMVs. Outer membrane vesicles from *E. coli* were purified as previously described (Hug and Feldman, 2011; Mashburn and Whiteley, 2005; Schertzer and Whiteley, 2012). In brief, *E. coli* strains were grown to stationary phase and pelleted. The cell supernatants were filtered using a 0.45 nm syringe filter and centrifuged at 346249×g for 1 h at 4° C. The pellet was resuspended in MV buffer (50 mM Tris pH=7.2, 5 mM NaCl, and 1 mM $MgSO_4$) and centrifuged at 346249×g for 1 h at 15° C. The vesicles were then washed in MV buffer and protein concentration was quantified using Coomassie Plus (Bradford) assay (Thermo).

Example 2

Engineering a Carbohydrate Antigen Based Vaccine Platform

While most infectious agents express surface proteins that can be targeted in vaccines, most pathogens also express carbohydrates on their surface. Glycoconjugate vaccines, such as those to *Streptococcus pneumoniae* capsule can prevent bacterial infections (De Roux et al., 2008). Using the bacterial adjuvant system described in patent US20130230555 A1, a system was developed to directly conjugate carbohydrates to the core region of *E. coli* lipopolysaccharide (FIG. 6A). The O-antigen region of *V. cholerae* lipopolysaccharide can be targeted by antibodies to prevent infection (Alam et al., 2014). The *V. cholerae* O-antigen coding sequences have been cloned into plasmid pPM1001 and O-antigen has been detected on the lipopolysaccharide of DH1 *E. coli* (FIG. 4B) (Manning et al., 1986). To engineer an *E. coli* strain that produced MPL directly conjugated to the *V. cholerae* O-antigen, the rfbD gene of *E. coli* was deleted from the genome, presumably because it disrupts *V. cholerae* O-antigen biosynthesis in *E. coli*, Co-expression of pPM1001 and pELOP in the ArfbD background allowed synthesis of the *V. cholera* O-antigen on *E. coli* lipopolysaccharide; however, the wild-type background did not produce the O-antigen. Surface exposure of the O-antigen was confirmed by using a *V. cholerae* O-antigen specific FITC-conjugated antibody (FIG. 6C). Last, lipid A was isolated and MALDI-TOF mass spectrometry indicated that a mixture of lipid was present that included the FDA-approved monophosphoryl lipid A with an m/z of 1729.1 (FIG. 6D). Also present was a dephosphorylated (lpxE) and deacylated (pagL) species corresponding to 1489.8 and a dephosphorylated (lpxE) and acylated (pagP) species corresponding to m/z 1954.4 (FIG. 6D).

Example 3

Figure 2A:
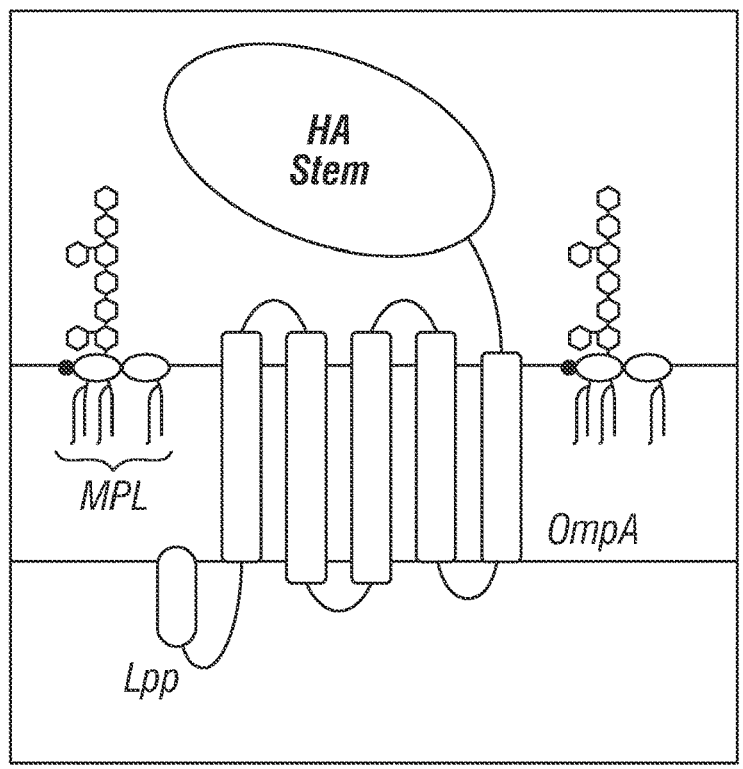
FIGS. 2A-D. Engineering a protein-based antigen/adjuvant vaccine delivery platform. (A) An illustration of a fusion protein containing an N-terminal outer membrane lipoprotein sorting sequence (Lpp), a transmembrane domain (OmpA) fused to a C-terminal influenza hemagglutinin (HA) containing the conserved HA2 domain is localized to the outer membrane of *E. coli* with the MPL adjuvant. (B) Western blot analysis of the Lpp-OmpA construct and the tripartite Lpp-OmpA-HA fusion protein from whole cells and isolated OMVs. (C) *E. coli* cells expressing the tripartite Lpp-OmpA-HA2 protein on the surface of the cells. A FITC-labeled secondary antibody was used to detect the surface localized HA2 protein. (D) MALDI-TOF mass spectrometry of lipid A isolated from *E. coli* cells.
Figure 2B:
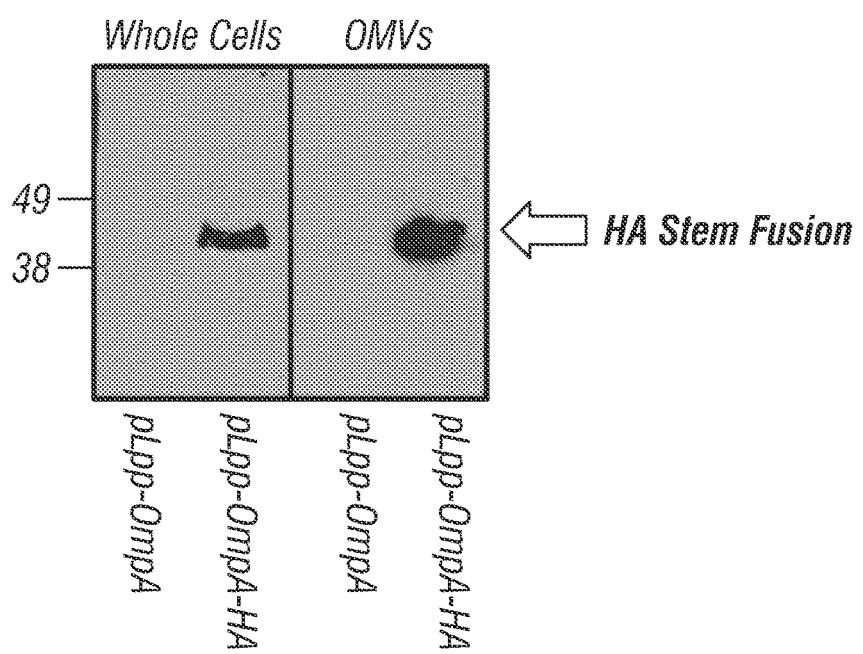
Figure 2C:
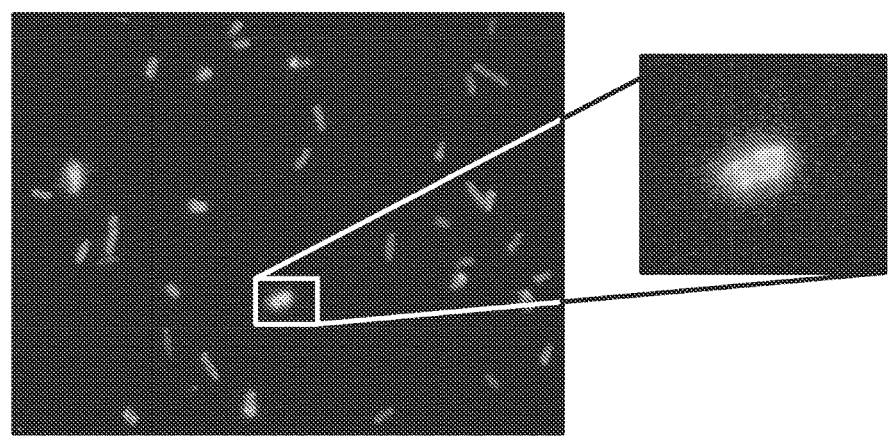
Figure 2D:
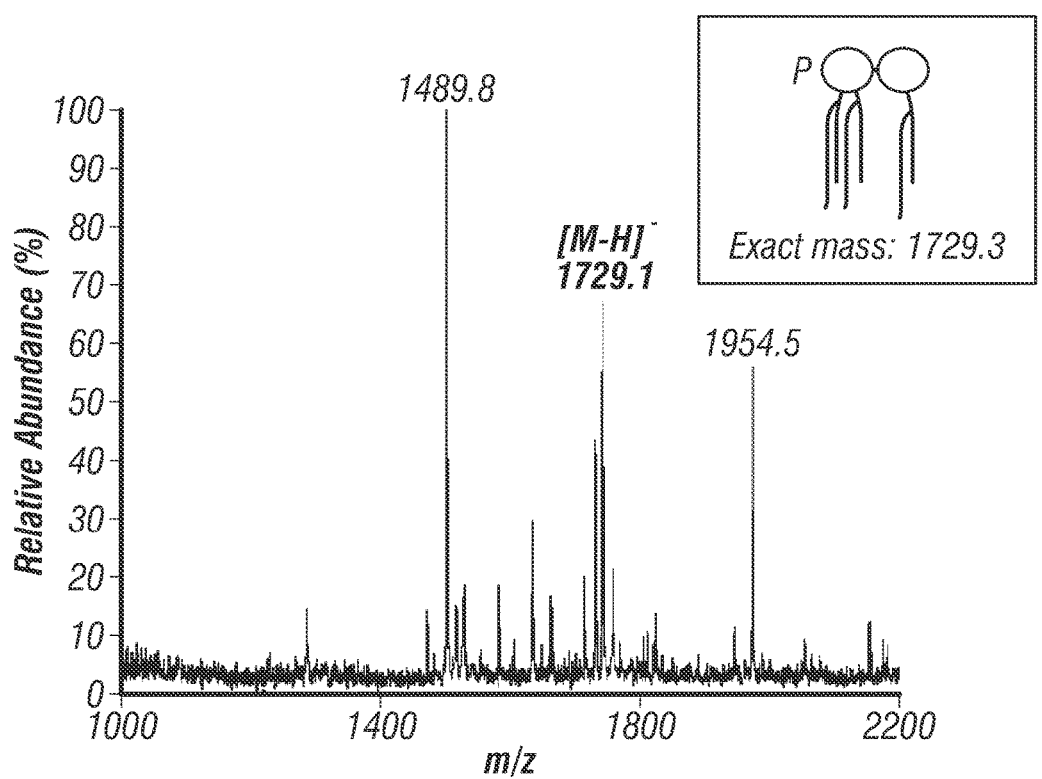
Figure 4A:
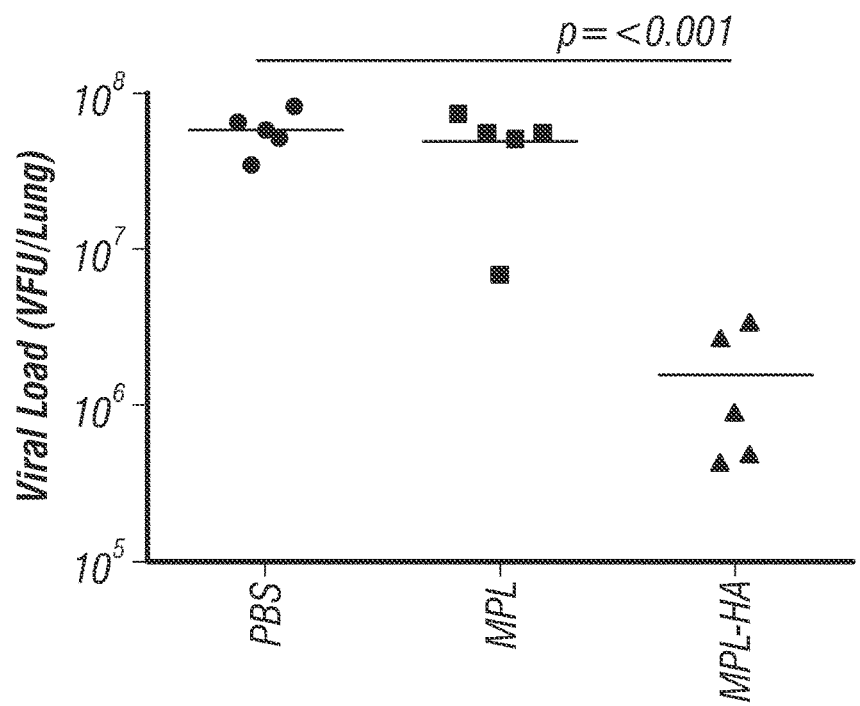
FIGS. 4A-D. Vaccination protects mice from influenza challenge. (A) Oral vaccination of mice with PBS, *E. coli* expressing MPL and the surface localized Lpp-OmpA protein (MPL), or *E. coli* expressing MPL and the surface localized tripartite Lpp-OmpA-HA protein (MPL-HA). (B) Intranasal vaccination of mice with PBS, OMVs isolated from *E. coli* expressing MPL and the surface localized Lpp-OmpA protein (MPL), OMVs isolated from *E. coli* expressing MPL and the surface localized tripartite Lpp-OmpA-HA protein (MPL-HA) or BPL-inactivated virus. (C) Survival curve of challenged mice after vaccination. (D) ELISA using sera from each group to detect recombinant HA2 protein.
Figure 4B:
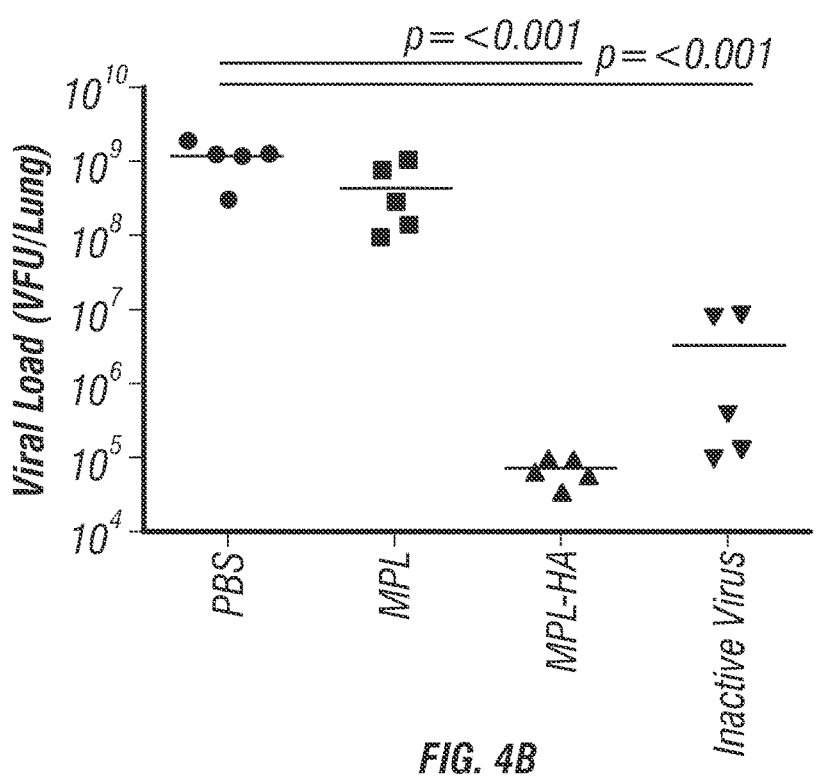
Figure 4C:
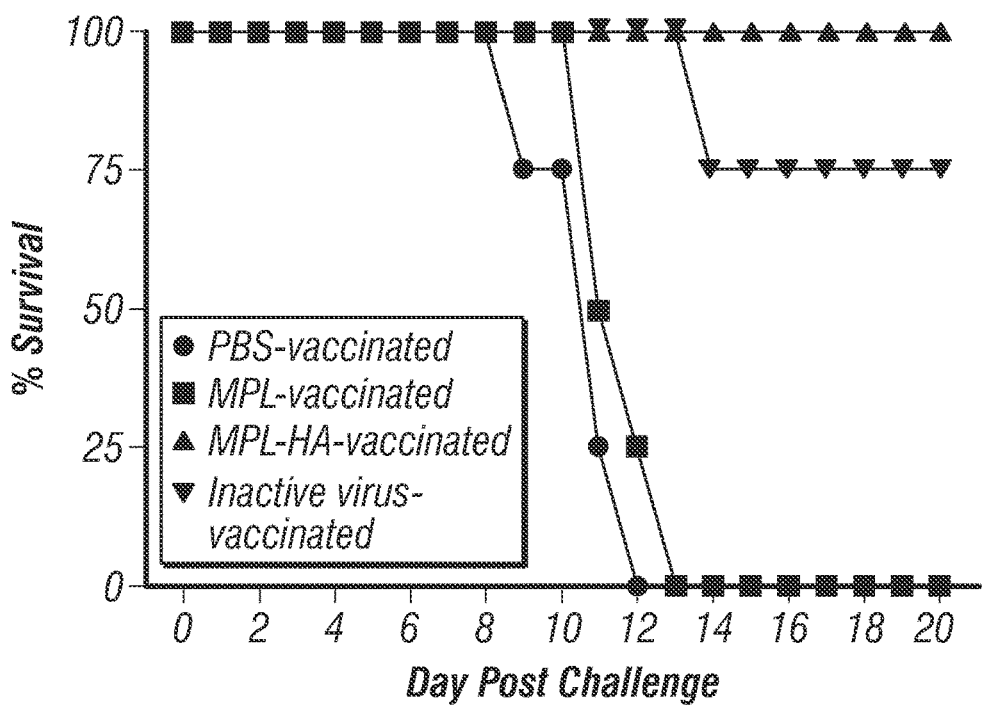
Figure 4D:
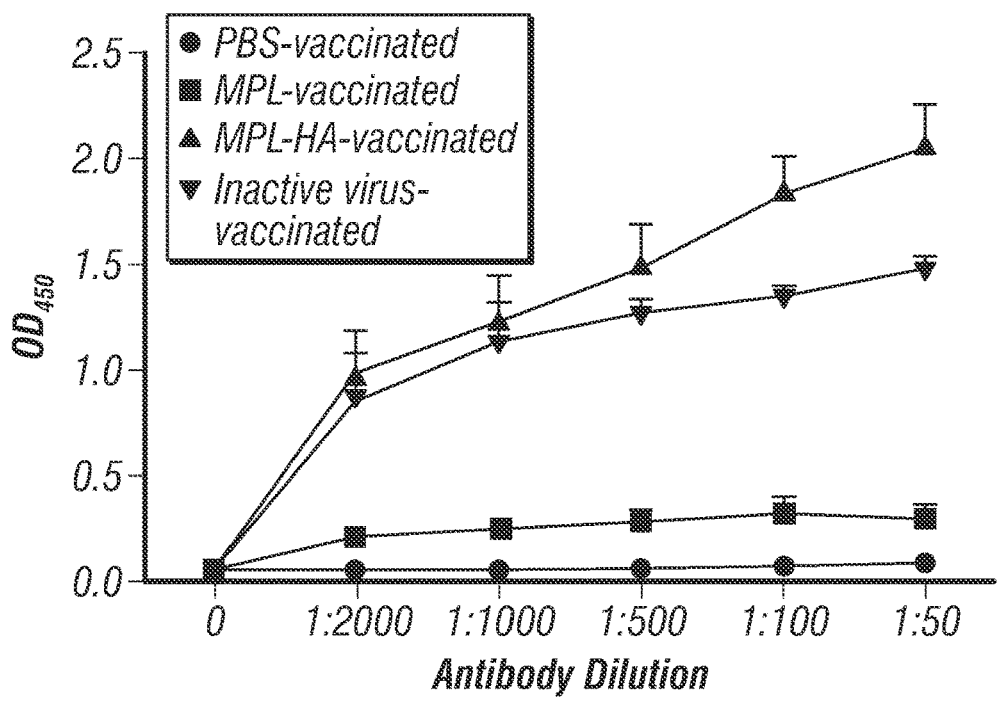
Figure 5D:
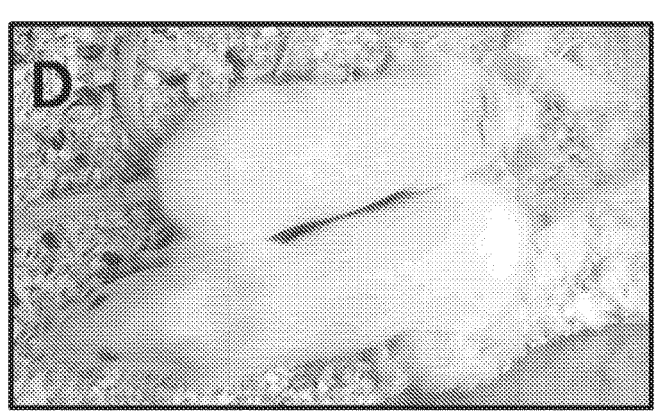
Figure 5E:
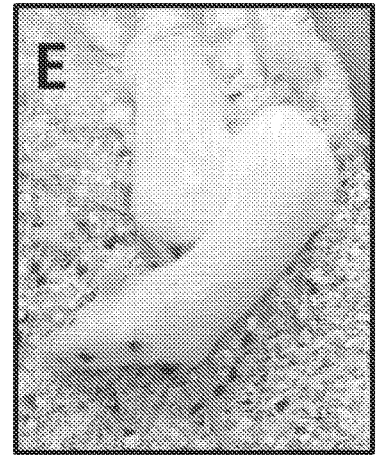

Plasmids and *E. coli* Strains for the Preparation of Lipid A/Influenza Polypeptide Vaccines The pQLinkN plasmids containing the various combinations of the lipid A modification genes lpxE, lpxF, lpxO, lpxR, pagL, and pagP as described in U.S. Patent Application Publication No. 2013/0230555 and Example 1 above were provided. Genes encoding the influenza hemagglutinin (HA) protein from Influenza strain A/PR/8/34 H1N1 (ACCESSION NP_040980.1 and NP_040981.1) and A/HK/03V6205/2003 H3N2 (ACCESSION EU502208 and EU516332.1) were introduced into these Lipid A modification enzyme encoding pQLinkN plasmids along with genes encoding Lpp signal sequence and OmpA polypeptides. See U.S. Pat. No. 5,348,867, which is hereby incorporated by reference in its entirety, for descriptions and sequences of the Lpp signal sequence and OmpA polypeptides.

More specifically, the genes encoding the above-described HA proteins were codon optimized by Genescript for optimal expression in *E. coli*, In order to target the conserved regions of the HA proteins, the genes included polypeptides encoding the HA2 domains for the H1N1 and H3N2 influenza viruses that were codon optimized by Genescript as previously described (Bommakanti et al., 2010; Bommakanti et al., 2012). The HA2 subunit of the hemagglutinin protein is well known to those of ordinary skill in the art as being created upon cleavage of hemagglutinin by cellular proteases. In some embodiments, a codon optimized polypeptide encoding amino acid residues 1-172 or 1-160 of HA2 is introduced into the pQLinkN plasmid. All genes were engineered with a 5' EcoRI site, a 3' BamHI site, and a C-terminal 6×-histidine tag.

After amplification of the coding sequences, DNA fragments were digested with EcoRI and BamHI and cloned into EcoRI- and BamHI-digested pTX101, Plasmid pTX101 is disclosed in U.S. Pat. No. 5,348,867, which is hereby incorporated by reference in its entirety. pTX101 fuses the target influenza protein to the C-terminus of an Lpp-OmpA protein fusion (Francisco et al., 1992). The tripartite fusion protein localizes to the *E. coli* outer membrane and surface displays the C-terminal influenza protein to the extracellular environment. The tripartite Lpp-OmpA-influenza protein coding sequence was amplified from pTX101 with primers that engineer 5' BamHI and 3' NotI restriction sites. Following the BamHI/NotI digestion, genes encoding the complete tripartite influenza fusion were cloned into BamHI/NotI-digested pQlinkN plasmid to allow expression from an IPTG-inducible promoter, resulting in co-expression of the Lipid A modification enzymes and the tripartite Lpp-OmpA-influenza protein.

These pQLinkN plasmids, which encode both the lipid A modification enzymes and the tripartite influenza fusion, were transformed into a W3110 *E. coli* strain mutated as follows. Deletions of pagP, lpxT and eptA resulted in a strain producing >95% of the prototypical, hexa-acylated bis-phosphorylated lipid A species (Needham et al., 2013). To increase production of outer membrane vesicles (OMVs), the gene Eck1763, which encodes the major outer membrane lipoprotein Lpp was also deleted from the *E. coli* genome. Deletion of the Lpp lipoprotein resulted in a 100- to 1000-fold increased production of OMVs in *E. coli* strains. *E. coli* W3110 gene deletions and antibiotic cassette removals were performed by P1 vir phage transduction using Keio mutants, as previously described (Baba et al., 2006; Touze et al., 2008). All *Escherichia coli* W3110 strains (mutated or wild-type) were grown from freezer stock on Luria-Bertani Broth (LB) or 2× Nutrient broth with 5 g/L of NaCl at 25° C., 30° C., or 37° C. and supplemented with 100 μg/mL ampicillin, 15 μg/mL chloramphenicol, or 30 μg/mL kanamycin when appropriate. When required, 50 μM-1 mM isopropyl β-D-1-thiogalactopyranoside (IPTG) was added as determined by TLC analysis of lipid A enzyme activity (Needham et al., 2013).

The above-described *E. coli* strain produced surface-exposed influenza proteins that were packaged into OMVs with the modified lipid A species. Outer membrane vesicles from *E. coli* were purified as previously described (Mashburn and Whiteley, 2005; Schertzer and Whiteley, 2012). In brief, *E. coli* strains were grown to stationary phase and pelleted. The cell supernatants were filtered using a 0.45 μm syringe filter and centrifuged at 346249×g for 1 h at 4° C. The pellet was resuspended in MV buffer (50 mM Tris pH=7.2, 5 mM NaCl, and 1 mM $MgSO_4$) and centrifuged at 346249×g for 1 hour at 15° C. The vesicles were then washed in MV buffer and protein concentration was quantified using Coomassie Plus (Bradford) assay (Thermo).

Example 4

Engineering a Protein Antigen Based Vaccine Platform

Nonpathogenic *E. coli* have been engineered to co-produce lipid A adjuvants and either protein or carbohydrate antigens on the surface of the bacterial cell. These vaccine components can be purified from the bacteria as OMVs and used as vaccines. Influenza was used herein to demonstrate the efficacy of this system. As a model for the vaccine, the HA2 domain of influenza hemagglutinin protein was co-localized to the surface of the bacterial strain by fusing it with an N-terminal Lpp sorting sequence and an OmpA domain (FIG. 2A) (Francisco et al., 1992; Georgiou et al., 1996). The Lpp sorting sequence and OmpA domains are membrane bound while the 6×his-tagged HA2 influenza protein is fused to the surface exposed loop at Asn159 through a Gly-Ile-Pro-Gly linker (FIG. 3A). This construct firmly anchors the HA2 protein onto the surface of the cell. For this study, the tripartite Lpp-OmpA-HA2 protein was linked into the pQlink plasmid system with the plasmid pELOP from U.S. Pat. Publn. No. US20130230555 for co-expression in *E. coli* to engineer expression of the HA2 antigen with the Federal Drug Administration approved monophosphoryl lipid A adjuvant on the surface of the cell (FIG. 2A) (Needham et al., 2013). Whole cells expressing this construct were isolated and separated using SDS-PAGE. Proteins were transferred to a nitrocellulose membrane and probed with an anti-5×-his antibody (Qiagen). The antibody detected the tripartite HA2 fusion protein at the correct molecular weight of 45.54 kD (FIG. 2B). Furthermore, a mutation was introduced into the background BN1 strain that genetically deleted the native Lpp sequence from the genome. This mutation has been shown to result in excess production of OMVs. Purified OMVs from the strain co-expressing the tripartite HA2 fusion and pELOP also contained high levels of the tripartite fusion protein as detected by Western blot (FIG. 2B). To confirm surface accessibility of the HA2 protein on the surface of the cell, bacteria were grown and labeled with a secondary antibody conjugated to a FITC molecule. These bacteria fluoresced indicating the localization of the HA2 protein onto the surface of the bacterial cell (FIG. 2C). Last, lipid A was isolated from this strain and MALDI-TOF Mass spectrometry indicated that a mixture of lipid was present that included the FDA-approved monophosphoryl lipid A with an m/z of 1729.1 (FIG. 2D). Also present was a dephosphorylated (via LpxE) and deacylated (via PagL) species corresponding to 1489.8 and a dephosphorylated and acylated (via LpxE and PagP) species corresponding to m/z 1954.4 (FIG. 2D). The tripartite HA2 constructs that we used are indicated in FIGS. 3A and 3B.

Example 5

Efficacy of the Protein Antigen Vaccine Platform in a Mouse Vaccination Model Either whole bacteria or purified OMVs were used to vaccinate eight week old mice on day 0 and boost on day 28, A subset of mice were used to collect serum before challenge and all other mice were challenged with a lethal dose of mouse-adapted H1N1 influenza virus on day 44, Animals were sacrificed seven days post infection and homogenized lung tissue was used to determine viral infectivity (FIG. 3C).

First, mice (n=5) were orally vaccinated with either PBS and whole *E. coli* that were producing the MPL adjuvant only or MPL and the HA2 expression construct. Upon sacrifice, titers indicted almost a 100-fold decrease in infectious viral load of the lungs suggesting that oral vaccination with whole bacteria could protect from influenza infection (FIG. 4A). Furthermore, OMVs were purified from bacteria containing the MPL or MPL-HA2 constructs. Mice vaccinated with the MPL-HA2 constructs had 10,000-fold less infectious influenza particles in their lungs after seven days when compared to MPL-vaccinated or PBS vaccinated mice. In addition, the MPL-HA2 construct protected the mouse lungs from influenza infection better than when an inactivated-influenza virus was used as the vaccine (FIG. 4B). The lung viral loads strongly correlate with survival of the mice, where those vaccinated with MPL-HA and inactive virus survived, but the PBS and MPL-vaccinated mice all died (FIG. 4C). Last, ELISAs were performed using serum isolated from each group. Mice vaccinated with MPL-HA2 and inactivated virus had antibodies that recognized the purified HA2 protein, whereas the MPL- and PBS-vaccinated mice did not (FIG. 4D).

The weight of all mice groups was monitored for up to seventeen days post-challenge. The PBS and MLP-vaccinated groups rapidly lost weight and infection manifested as a ruffled coat, lethargy, and dehydration post challenge (FIGS. 5A-C). In contrast the MPL-HA2 and inactivated virus-vaccinated groups recovered fully from the challenge and maintained a healthy coat (FIGS. 5A, 5D, and 5E).

Example 6

Plasmids and *E. coli* Strains for the Preparation of Carrier Protein/Polysaccharide Antigen To engineer glycoprotein vaccines, acrA (cjj0390) and pglB (cjj1143) genetic coding sequences are amplified from *Campylobacter jejuni* 81-176 with BamHI and NotI sites and cloned into BamHI and NotI-digested pQlinkN for expression from an IPTG-inducible promoter (Scheich et al., 2007). A C-terminal 6×-histidine tag is engineered onto the acrA coding sequence. AcrA is an acceptor protein that is glycosylated by the ligase Pg1B in *C. jejuni* (Feldman et al., 2005). The two genes, acrA and pglB are linked into the same vector for co-expression as previously described (Scheich et al., 2007; Ihssen et al., 2010). The acrA and pglB genes and their IPTG-inducible promoters are then amplified from the pQlinkN-derived vector with SalI sites and cloned into SalI-digested pACYC184.

The *V. cholerae* O-antigen plasmid pPM1001 described in Example 1 above is then provided and both the pPM1001 plasmid and the pACYC184 plasmid containing acrA and pglB genes are transformed into an *E. coli* strain having the following characteristics: All *E. coli* W3110 strains are grown from freezer stock on Luria-Bertani Broth (LB) or 2× Nutrient broth with 5 g/L of NaCl at 25° C., 30° C., or 37° C. and supplemented with 100 μg/mL ampicillin, 15 μg/mL chloramphenicol, or 30 μg/mL kanamycin when appropriate. When required 50 μM-1 mM isopropyl β-D-1-thiogalactopyranoside (IPTG) is added as determined by TLC analysis of lipid A enzyme activity (Needham et al., 2013). For optimal expression of O-antigen/capsule genes in *E. coli*, either the rfbD gene (Eck2034) or the entire *E. coli* O-antigen biosynthetic genetic region from rfbB to wbbL (Eck2025-Eck2035) are chromosomally deleted by P1 vir phage transduction using Keio mutants or lambda red recombination, respectively (Baba et al., 2006; Touze et al., 2008). For production of all glycoprotein vaccines, efficient ligation of polysaccharides (O-antigen or capsule) onto an acceptor protein, called AcrA (Cjj0390) by the ligase Pg1B (Cjj1143) requires deletion of the *E. coli* gene encoding WaaL (Eck3612).

Once transformed into the *E. coli* as described above, the *V. cholerae* O-antigen plasmid pPM1001 is co-expressed with the pACYC-derived plasmid with IPTG to ligate the *V. cholerae* O-antigen onto the AcrA protein. AcrA glycoproteins are purified using Ni-affinity chromatography and size exclusion chromatography for use as glycoconjugate vaccines. A similar method is used to generate other O-antigen (*S. typhimurium, Shigella*) and capsule (*S. pneumoniae, S. aureus*) glycoprotein vaccines using their respective plasmids, which plasmids are described in the Examples above.

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alam et al., Evaluation in Mice of a Conjugate Vaccine for Cholera Made from *Vibrio cholerae* O1 (Ogawa) O-Specific Polysaccharide. *PLoS Negl. Trop. Dis.,* 8:e2683, 2014.

Baba et al., Construction of *Escherichia coli* K-12 in-frame, single-gene knockout mutants: the Keio collection. *Mol. Syst. Biol.,* 2:2006.0008, 2006.

Bommakanti et al., Design of an HA2-based *Escherichia coli* expressed influenza immunogen that protects mice from pathogenic challenge. *Proc. Natl. Acad. Sci. U.S.A.,* 107:13701-13706, 2010.

Bommakanti et al., Design of *Escherichia coli*-Expressed Stalk Domain Immunogens of H1N1 Hemagglutinin That Protect Mice from Lethal Challenge. *J. Virol.,* 86:13434-13444, 2012.

Bullough et al., Structure of influenza haemagglutinin at the pH of membrane fusion. *Nature,* 371:37-43, 1994.

Chen et al., Structure of the hemagglutinin precursor cleavage site, a determinant of influenza pathogenicity and the origin of the labile conformation. *Cell,* 95:409-417, 1998.

Cox, Pandemic influenza: overview of vaccines and antiviral drugs. *Yale J. Biol. Med.,* 78:321-328, 2005.

De Roux et al., Comparison of pneumococcal conjugate polysaccharide and free polysaccharide vaccines in elderly adults: conjugate vaccine elicits improved antibacterial immune responses and immunological memory. *Clin. Infect. Dis.,* 46:1015-1023, 2008.

Ekiert et al., Antibody recognition of a highly conserved influenza virus epitope. *Science,* 324:246-251, 2009.

Fan et al., Preclinical study of influenza virus A M2 peptide conjugate vaccines in mice, ferrets, and rhesus monkeys. *Vaccine,* 22:2993-3003, 2004.

Feldman et al., Engineering N-linked protein glycosylation with diverse O antigen lipopolysaccharide structures in *Escherichia coli. Proc. Natl. Acad. Sci. U.S.A.,* 102:3016-3021, 2005.

Francisco et al., Transport and anchoring of beta-lactamase to the external surface of *Escherichia coli. Proc. Natl. Acad. Sci. U.S.A.,* 89:2713-2717, 1992.

Georgiou et al., Display of β-lactamase on the *Escherichia coli* surface: outer membrane phenotypes conferred by Lpp'-OmpA'-β-lactamase fusions. *Protein Eng.,* 9:239-247, 1996.

Gocnik et al., Antibodies induced by the HA2 glycopolypeptide of influenza virus haemagglutinin improve recovery from influenza A virus infection. *J. Gen. Virol.,* 89:958-967, 2008.

Hankins et al., Elucidation of a novel *Vibrio cholerae* lipid A secondary hydroxy-acyltransferase and its role in innate immune recognition. *Mol. Microbiol.,* 81:1313-1329, 2011.

Harris et al., Cholera. *Lancet,* 379:2466-2476, 2012.

Horimoto and Kawaoka, Influenza: lessons from past pandemics, warnings from current incidents. *Nat. Rev. Microbiol.,* 3:591-600, 2005.

Hug and Feldman, Analogies and homologies in lipopolysaccharide and glycoprotein biosynthesis in bacteria. *Glycobiology,* 21:138-151, 2011.

Ihssen et al., Production of glycoprotein vaccines in *Escherichia coli. Microbial Cell Factories,* 9:61-74, 2010.

Kaper et al., Cholera. *Clin. Microbiol. Rev.,* 8:48-86, 1995.

Lam et al., Outer surface proteins E and F of *Borrelia burgdorferi*, the agent of Lyme disease. *Infect. Immun.,* 62:290-298, 1994.

Lamb and Krug, Orthomyxoviridae: The viruses and their replication., 2001, pp. 1487-1531. In *Fields Virology*, 4th ed., 4th ed. Lippincott, Williams and Wilkins, Philadelphia Pa.

Manning et al., Molecular cloning and expression in *Escherichia coli* K-12 of the O antigens of the Inaba and Ogawa serotypes of the *Vibrio cholerae* O1 lipopolysaccharides and their potential for vaccine development. *Infect. Immun.,* 53:272-277, 1986.

Mashburn and Whiteley, Membrane vesicles traffic signals and facilitate group activities in a prokaryote. *Nature,* 437:422-425, 2005.

Needham et al., Modulating the innate immune response by combinatorial engineering of endotoxin. *Proc. Natl. Acad. Sci. U.S.A.,* 110:1464-1469, 2013.

Nicolay et al., *Crit. Rev. Microbiol.,* 41(1):109-123, 2015

Okuno et al., A common neutralizing epitope conserved between the hemagglutinins of influenza A virus H1 and H2 strains. *J. Virol.,* 67:2552-2558, 1993.

Okuno et al., Protection against the mouse-adapted A/FM/1/47 strain of influenza A virus in mice by a monoclonal antibody with cross-neutralizing activity among H1 and H2 strains. *J. Virol.,* 68:517-520, 1994.

Sánchez-Fauquier et al., Isolation of cross-reactive, subtype-specific monoclonal antibodies against influenza virus HA1 and HA2 hemagglutinin subunits. *Arch. Virol.,* 97:251-265, 1987.

Sauter et al., Binding of influenza virus hemagglutinin to analogs of its cell-surface receptor, sialic acid: analysis by proton nuclear magnetic resonance spectroscopy and X-ray crystallography. *Biochemistry,* 31:9609-9621, 1992.

Scheich et al., Vectors for co-expression of an unrestricted number of proteins. *Nucleic Acids Res.,* 35:e43, 2007.

Schertzer and Whiteley, A Bilayer-Couple Model of Bacterial Outer Membrane Vesicle Biogenesis. *mBio,* 3:e00297-11, 2012.

Seed et al., Phase variable O antigen biosynthetic genes control expression of the major protective antigen and bacteriophage receptor in *Vibrio cholerae* O1. *PLoS Pathog.,* 8:e1002917, 2012.

Skehel and Wiley, Receptor binding and membrane fusion in virus entry: the influenza hemagglutinin. *Annu. Rev. Biochem.,* 69:531-569, 2000.

Smirnov et al., Prevention and treatment of bronchopneumonia in mice caused by mouse-adapted variant of avian H5N2 influenza A virus using monoclonal antibody against conserved epitope in the HA stem region. *Arch. Virol.,* 145:1733-1741, 2000.

Sui et al., Structural and functional bases for broad-spectrum neutralization of avian and human influenza A viruses. *Nat. Struct. Mol. Biol.,* 16:265-273, 2009.

Throsby et al., Heterosubtypic neutralizing monoclonal antibodies cross-protective against H5N1 and H1N1 recovered from human IgM+ memory B cells. *PLoS ONE,* 3:e3942, 2008.

What is claimed is:

1. An isolated engineered bacteria strain comprising
   (a) at least one expression vector comprising at least one polynucleotide encoding a lipid A modification enzyme, wherein the gene encoding a lipid A modification enzyme is selected from the group consisting of lpxE, lpxF, lpxO, lpxR, pagL, and pagP; and
   (b) at least one expression vector comprising at least one polynucleotide encoding a polysaccharide antigen biosynthesis protein,
   wherein the engineered bacteria strain produces the polysaccharide antigen covalently conjugated to a modified lipid A; and
   wherein the engineered bacteria strain:
      (i) comprises a deletion of the Eck1673 gene;
      (ii) comprises at least lpxE, lpxO, pagL and pagP;
      (iii) produces the *Vibrio cholerae* O antigen, *Salmonella typhimurium* O antigen, or *Shigella spcs* O antigen antigen covalently conjugated to a modified lipid A; or
      (iv) produces the *Streptococcus pneumonia* capsule, *Staphylococcus aureus* capsule, or *Neisseria meningitidis* capsule antigen covalently conjugated to a modified lipid A.

2. The isolated engineered strain of claim 1, further comprising a deletion of the Eck1673 gene.

3. The isolated engineered strain of claim 1, further comprising a deletion of the rfbD gene.

4. The isolated engineered strain of claim 1, further comprising a deletion of the rfbB-wbbL genetic region.

5. The isolated engineered strain of claim 1, comprising at least lpxE, pagL and pagP.

6. The isolated engineered strain of claim 1, comprising at least lpxE, lpxO, pagL and pagP.

7. The isolated engineered strain of claim 1, wherein the polysaccharide antigen is *Vibrio cholerae* O antigen, *Salmonella typhimurium* O antigen, or *Shigella spcs* O antigen.

8. The isolated engineered strain of claim 7, wherein the at least one polynucleotide encoding a polysaccharide antigen biosynthesis protein is selected from the group consisting of a gmhD gene, a manC gene, a manB gene, a gmd gene, a wbeE gene, a wbeG gene, a wzm, a wzt gene, a wbeK gene, a wbeL gene, a wbeM gene, a wbeN gene, a wbeO gene, a wbeP gene, a wbeT gene, a wbeU gene, a wbeV gene, a gale gene, and a wbeW gene, and a wbf region gene.

9. The isolated engineered strain of claim 1, wherein the polysaccharide antigen is *Streptococcus pneumonia* capsule, *Staphylococcus aureus* capsule, or *Neisseria meningitidis* capsule.

10. The isolated engineered strain of claims 1, wherein the bacteria is an *E. coli* bacteria.

11. The isolated engineered strain of claim 9, wherein the at least one polynucleotide encoding a polysaccharide antigen biosynthesis protein is selected from the group consisting of a wzm gene, a wzt gene, a wzx gene, and a wzy gene.

12. A composition isolated from the engineered bacteria strain of claim 1, wherein the composition comprises the polysaccharide antigen covalently conjugated to a modified lipid A.

* * * * *

UNITED STATES PATENT AND TRADEMARK OFFICE
CERTIFICATE OF CORRECTION

PATENT NO. : 10,420,833 B2
APPLICATION NO. : 15/311233
DATED : September 24, 2019
INVENTOR(S) : M. Stephen Trent et al.

Page 1 of 1

It is certified that error appears in the above-identified patent and that said Letters Patent is hereby corrected as shown below:

On the Title Page

Item (86) 371 (c)(1), (2) Date:, delete "Feb. 13, 2017" and insert --Nov. 15, 2016-- therefor.

Signed and Sealed this
Twentieth Day of October, 2020

Andrei Iancu
*Director of the United States Patent and Trademark Office*